US010115192B2

(12) United States Patent
Watanabe et al.

(10) Patent No.: US 10,115,192 B2

(45) Date of Patent: Oct. 30, 2018

(54) APPARATUS AND METHOD FOR VISUALIZATION

(71) Applicants: FUJITSU LIMITED, Kawasaki-shi, Kanagawa (JP); The University of Tokyo, Tokyo (JP)

(72) Inventors: Masahiro Watanabe, Kawasaki (JP); Satoshi Fuchikami, Fukuoka (JP); Tadashi Ataka, Kawasaki (JP); Yoshimasa Kadooka, Kawasaki (JP); Toshiaki Hisada, Tokyo (JP); Seiryo Sugiura, Tokyo (JP); Takumi Washio, Tokyo (JP); Jun-ichi Okada, Tokyo (JP)

(73) Assignees: FUJITSU LIMITED, Kawasaki (JP); THE UNIVERSITY OF TOKYO, Tokyo (JP)

( * ) Notice: Subject to any disclaimer, the term of this patent is extended or adjusted under 35 U.S.C. 154(b) by 41 days.

(21) Appl. No.: 14/730,592

(22) Filed: Jun. 4, 2015

(65) Prior Publication Data

US 2015/0379755 A1 Dec. 31, 2015

(30) Foreign Application Priority Data

Jun. 25, 2014 (JP) ................................ 2014-129752

(51) Int. Cl.
*G06T 15/00* (2011.01)
*G06T 7/00* (2017.01)
(Continued)

(52) U.S. Cl.
CPC .......... *G06T 7/0012* (2013.01); *A61B 5/0452* (2013.01); *G06F 19/00* (2013.01); *G06T 19/00* (2013.01); *G16H 50/50* (2018.01)

(58) Field of Classification Search
CPC ................................ G06T 19/00; G06T 17/20
(Continued)

(56) References Cited

U.S. PATENT DOCUMENTS 5,273,038 A 12/1993 Beavin
5,803,084 A * 9/1998 Olson ................ A61B 5/04011 600/512

(Continued)

FOREIGN PATENT DOCUMENTS

JP 2007-313122 12/2007
JP WO 2007/146864 A2 12/2007
JP 2009-539566 11/2009

OTHER PUBLICATIONS

Wikipedia, "Electrical conduction system of the heart", version at Apr. 4, 2014, https://en.wikipedia.org/wiki/Electrical_conduction_system_of_the_heart.*

(Continued)

*Primary Examiner* — Jin Ge
(74) *Attorney, Agent, or Firm* — Staas & Halsey LLP

(57) ABSTRACT

Based on heart behavior data, a computation unit determines a first time step at which a heart exhibits a first behavior in response to a first wave of an electrical signal, as well as a second time step at which the heart exhibits a second behavior in response to a second wave of the same. The computation unit reproduces the heart's behavior over time by updating a three-dimensional model of the heart according to the heart behavior data, simultaneously with variations in electrical signal strength over time according to electrocardiogram data. The computation unit coordinates this reproduction such that a first shape of the heart at the first time is reproduced step simultaneously with the first wave of the electrical signal, and such that a second shape (Continued)

of the heart at the second time step is reproduced simultaneously with the second wave of the electrical signal.

4 Claims, 23 Drawing Sheets

(51) Int. Cl.
*G16H 50/50* (2018.01)
*A61B 5/0452* (2006.01)
*G06T 19/00* (2011.01)
*G06F 19/00* (2018.01)

(58) Field of Classification Search
USPC .......................................................... 345/419
See application file for complete search history.

(56) References Cited

U.S. PATENT DOCUMENTS

2007/0276274 A1 11/2007 Kawada et al.
2009/0088655 A1* 4/2009 Vajdic .................. A61B 5/0452 600/523
2009/0135992 A1 5/2009 Vaillant et al.
2010/0179446 A1* 7/2010 Bojovic ............. A61B 5/04011 600/512

OTHER PUBLICATIONS

"The Cardiovascular System: The Heart", http://classes.midlandstech.edu/carterp/Courses/bio211/chap18/chap18.html. vresion at Apr. 13, 2014.*
Sovilj, S., Magjarevic, R., Lovell, N.H. and Dokos, S. (2013) A simplified 3D model of whole heart electrical activity and 12-lead ECG generation. Computational and Mathematical Methods in Medicine, 2013, Article ID: 134208.*
Sovilj, S., Magjarevic, R., Lovell, N., Dokos, S. (2013). A simplified 3D model of whole heart electrical activity and 12-lead ECG generation.Computational and Mathematical Methods in Medicine, article ID 134208-10.*
Sermesant et al., "An Electromechanical Model of the Heart for Image Analysis and Simulation", IEEE Transactions on Medical Imaging, vol. 25, No. 5, May 1, 2006, pp. 612-625.
European Search Report dated Nov. 10, 2015 in European Patent Application No. 15170995.3.
Patent Abstracts of Japan, Publication No. 2007-313122, published Dec. 6, 2007.
Masashi Tsuyunashi et al., "The Holter ECG waveform classification using clustering," The Institute of Electronics, Information and Communication Engineers, Published Dec. 1, 2003, pp. 1-6, and related CiNii Articles Bibliographic data, downloaded Apr. 17, 2015 from http://ci.nii.ac.jp/naid/110003286587/en/
Japanese Office Action dated Jan. 23, 2018 in corresponding Japanese Patent Application No. 2014-129752.

* cited by examiner

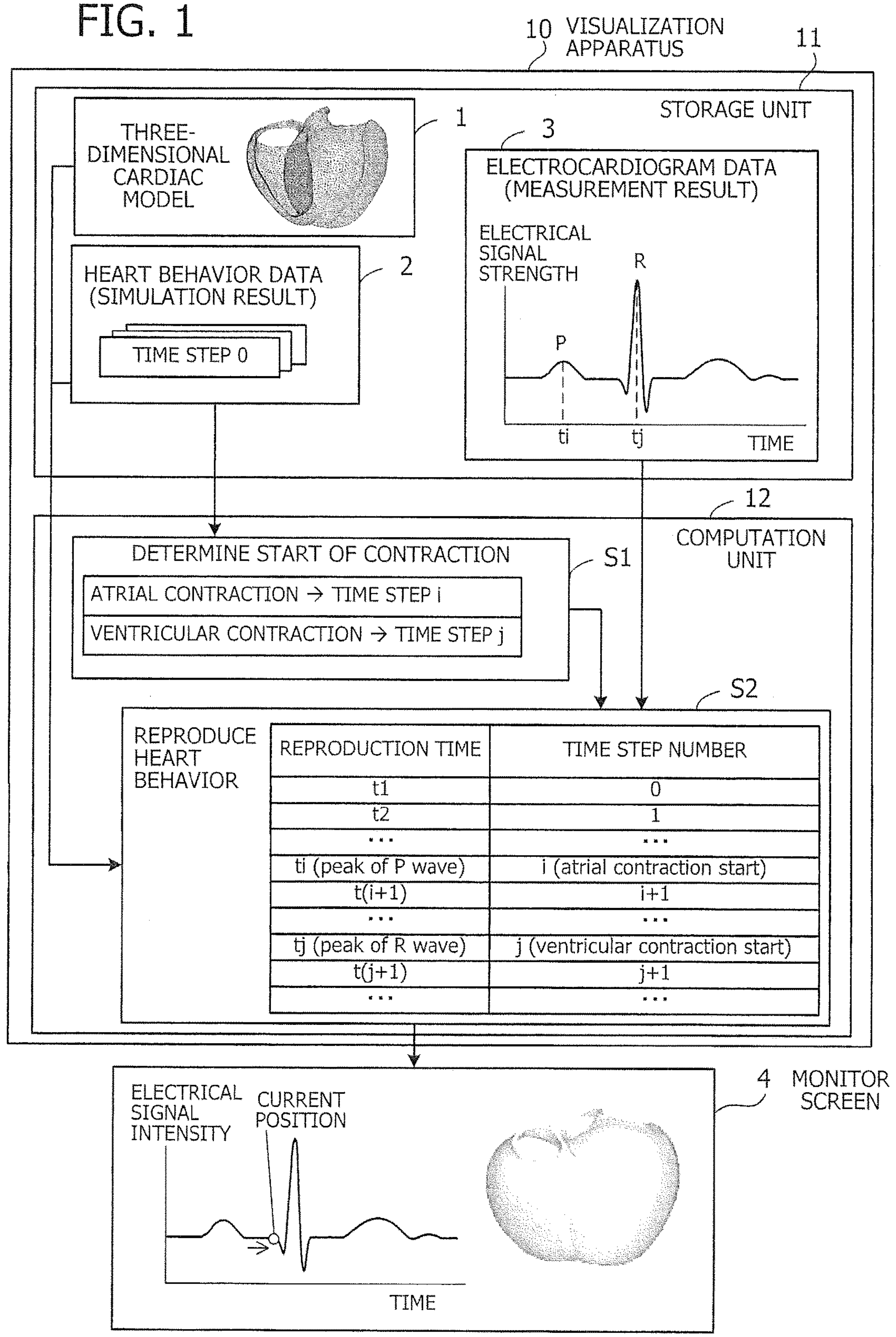
FIG. 1
10 VISUALIZATION APPARATUS
11
STORAGE UNIT
THREE-DIMENSIONAL CARDIAC MODEL
1
3
ELECTROCARDIOGRAM DATA (MEASUREMENT RESULT)
ELECTRICAL SIGNAL STRENGTH
R
P
ti
tj
TIME
HEART BEHAVIOR DATA (SIMULATION RESULT)
2
TIME STEP 0
12
COMPUTATION UNIT
DETERMINE START OF CONTRACTION
S1
ATRIAL CONTRACTION → TIME STEP i
VENTRICULAR CONTRACTION → TIME STEP j
S2
REPRODUCE HEART BEHAVIOR
REPRODUCTION TIME
TIME STEP NUMBER
t1
0
t2
1
ti (peak of P wave)
i (atrial contraction start)
t(i+1)
i+1
tj (peak of R wave)
j (ventricular contraction start)
t(j+1)
j+1
4 MONITOR SCREEN
ELECTRICAL SIGNAL INTENSITY
CURRENT POSITION
TIME

| TIME STEP#0 | | | | |
|---|---|---|---|---|
| ELEMENT ID & NODE ID | POSITION | PHYSICAL QUANTITY A | PHYSICAL QUANTITY B | ··· |
| ELEMENT1 | (x1,y1,z1) | data11 | data21 | ··· |
| ELEMENT2 | (x2,y2,z2) | data12 | data22 | ··· |
| ELEMENT3 | (x3,y3,z3) | data13 | data23 | ··· |
| ··· | ··· | ··· | ··· | ··· |
| NODE1 | (x4,y4,z4) | data14 | data24 | ··· |
| NODE2 | (x5,y5,z5) | data15 | data25 | ··· |
| NODE3 | (x6,y6,z6) | data16 | data26 | ··· |
| ··· | ··· | ··· | ··· | ··· |

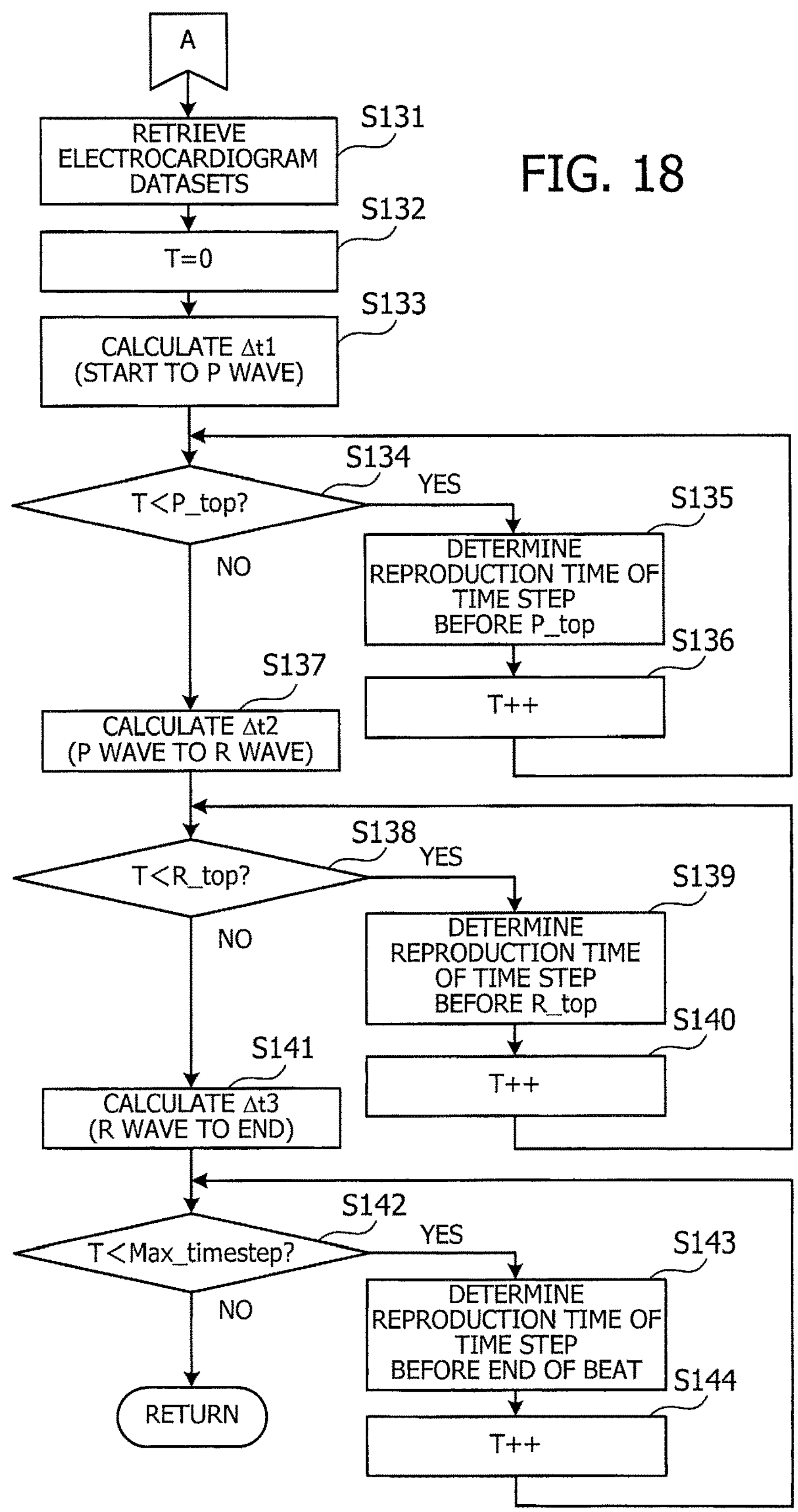

FIG. 18
A
RETRIEVE ELECTROCARDIOGRAM DATASETS
S131
T=0
S132
CALCULATE Δt1 (START TO P WAVE)
S133
T<P_top?
S134
YES
NO
DETERMINE REPRODUCTION TIME OF TIME STEP BEFORE P_top
S135
T++
S136
CALCULATE Δt2 (P WAVE TO R WAVE)
S137
T<R_top?
S138
YES
NO
DETERMINE REPRODUCTION TIME OF TIME STEP BEFORE R_top
S139
T++
S140
CALCULATE Δt3 (R WAVE TO END)
S141
T<Max_timestep?
S142
YES
NO
DETERMINE REPRODUCTION TIME OF TIME STEP BEFORE END OF BEAT
S143
T++
S144
RETURN

FIG. 19

151 SYNCHRONIZATION DATA

| TIME STEP NUMBER | REPRODUCTION TIME |
|---|---|
| 0 | t1 |
| 1 | t2 |
| 2 | t3 |
| ⋮ | ⋮ |
| i (P_top) | t11 |
| i+1 | t12 |
| i+2 | t13 |
| ⋮ | ⋮ |
| j (R_top) | t21 |
| j+1 | t22 |
| j+2 | t23 |
| ⋮ | ⋮ |

APPARATUS AND METHOD FOR VISUALIZATION

CROSS-REFERENCE TO RELATED APPLICATION

This application is based upon and claims the benefit of priority of the prior Japanese Patent Application No. 2014-129752, filed on Jun. 25, 2014, the entire contents of which are incorporated herein by reference.

FIELD

The embodiments discussed herein relate to an apparatus and method for visualizing behavior of a heart.

BACKGROUND

The recent advancement of computer-based numerical analysis has enabled reproduction of various phenomena in a heart by modeling it on a computer. For example, the behavior of myocardium is analyzed numerically and reproduced on a monitor screen with the techniques of three-dimensional computer graphics. It is also possible to produce an electrocardiogram on the thorax of a person as an outcome of simulation. Such output data representing electrical activities in a heart may be visualized as video images, along with other data indicating the propagation of cardiac excitation.

Electrocardiograms are used as source data for analysis of arrhythmia and other heart diseases. For example, one proposed electrocardiogram analyzer evaluates electrical activities in a heart in terms of the distribution of indicators that are useful for prediction of fatal arrhythmias. Also, several researchers have proposed a method for classifying waveforms of Holter electrocardiography by using clustering techniques. See, for example, the following documents:

Japanese Laid-open Patent Publication No. 2007-313122

Tsuyunashi, Oguri, Matsuo, Iwata, "The Holter ECG waveform classification using clustering," The Institute of Electronics, Information and Communication Engineers (IEICE), Technical Report of IEICE. MBE, ME and Biocybernetics, Dec. 1, 2003, 103(489), pp. 23-28

A patient suspected of having a heart disease is subjected to monitoring of electrical signals produced in his or her myocardium, and the result is obtained as electrocardiogram data. There is a need in some situations for visually checking the behavior of the heart in comparison with electrocardiogram data. This is achieved by conducting a dynamic simulation of myocardial motion and blood flows and reproducing the simulated heart behavior in the form of a three-dimensional model on a monitor screen.

It is not easy, however, for the conventional tools to make a simulation result exactly simultaneous with electrocardiogram data because of their difference in the progress of time. More specifically, existing electrocardiogram data is used as input data for a behavioral simulation of myocardium, where the electrocardiogram data provides particular conditions about propagation of excitation in the patient's heart. The simulation process produces a set of output data indicating the state of the heart at each discrete time step. There is, however, some amount of time difference between the generation of electrical signals seen in the electrocardiogram and the consequent contraction of myocardium. Because of this time difference, simply starting an electrocardiogram together with animation of a heart beat would not be sufficient for achieving correct synchronization between the variations of electrical signal strength and the motion of cardiac muscle.

SUMMARY

In one aspect of the embodiments, there is provided a visualization apparatus that includes a memory and a processor. The memory is configured to store a three-dimensional model of a heart of a patient, heart behavior data representing shapes of the heart at different time steps of a behavioral simulation of the heart, and electrocardiogram data representing temporal variations of an electrical signal in myocardium that have been measured from the patient. The processor is configured to perform a procedure including: determining, based on the heart behavior data, a first time step at which the heart exhibits a first behavior in response to a first wave of the electrical signal, as well as a second time step at which the heart exhibits a second behavior in response to a second wave of the electrical signal; and reproducing behavior of the heart over time by updating the three-dimensional model according to the heart behavior data, simultaneously with variations in strength of the electrical signal over time according to the electrocardiogram data, such that a first shape of the heart at the first time step is reproduced simultaneously with the first wave of the electrical signal, and such that a second shape of the heart at the second time step is reproduced simultaneously with the second wave of the electrical signal.

The object and advantages of the invention will be realized and attained by means of the elements and combinations particularly pointed out in the claims.

It is to be understood that both the foregoing general description and the following detailed description are exemplary and explanatory and are not restrictive of the invention.

BRIEF DESCRIPTION OF DRAWINGS

FIG. 1 illustrates an exemplary functional structure of a visualization apparatus according to a first embodiment;

FIGS. 17 and 18 are first and second halves of a flowchart illustrating a procedure of producing synchronization data;

FIG. 19 illustrates an example of synchronization data;

DESCRIPTION OF EMBODIMENTS

Figure 2:
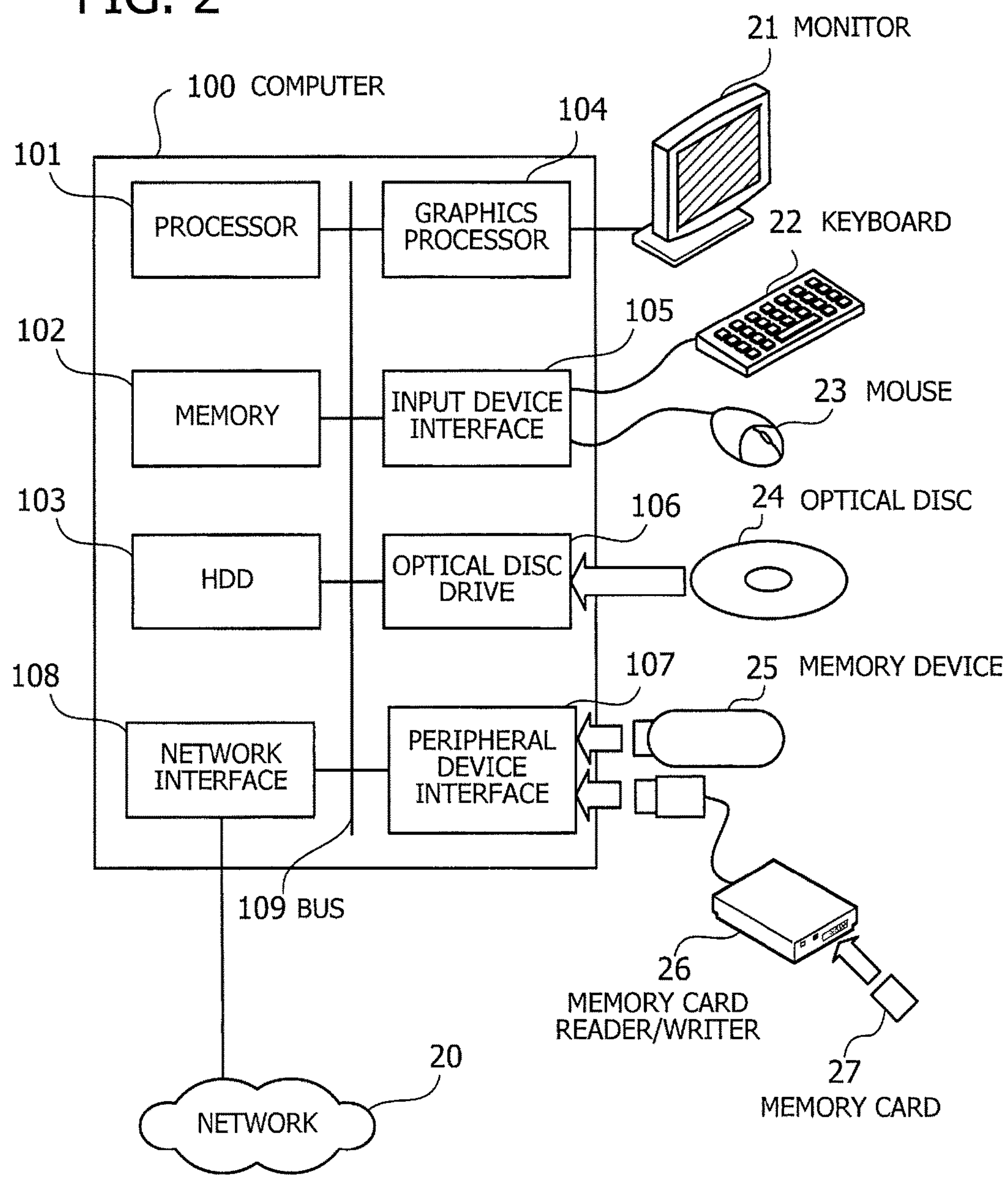
FIG. 2 illustrates an exemplary hardware configuration of a computer according to a second embodiment.

Several embodiments of the present invention will be described below with reference to the accompanying drawings. These embodiments may be combined with each other unless they have contradictory features.

(a) First Embodiment

This section describes a first embodiment. To start with, FIG. 1 illustrates an exemplary functional structure of a visualization apparatus according to a first embodiment. The illustrated visualization apparatus 10 includes a storage unit 11 and a computation unit 12.

The storage unit 11 stores a three-dimensional cardiac model 1, heart behavior data 2, and electrocardiogram data 3. The three-dimensional cardiac model 1 is a structure model representing a heart under analysis. The heart behavior data 2 represents shapes of the heart at different time steps of a behavioral simulation of the heart. For reproduction of simulated behavior of the heart, the time steps are labeled in their chronological order, with successively larger numbers starting from zero. The electrocardiogram data 3 represents temporal variations of an electrical signal in myocardium that have been measured from the patient's body. For example, the electrical signal is measured in terms of voltage.

Based on of the heart behavior data 2 noted above, the computation unit 12 determines a first time step at which the heart exhibits a first behavior in response to a first wave of the electrical signal, as well as a second time step at which the heart exhibits a second behavior in response to a second wave of the electrical signal (step S1). For example, the first wave is P wave seen in an electrocardiogram given by the electrocardiogram data 3, and the first time step refers to the moment when the atriums begin to contract. The second wave is, on the other hand, R wave seen in the electrocardiogram, and the second time step refers to the moment when the ventricles begin to contract.

The computation unit 12 reproduces behavior of the heart over time by updating the three-dimensional cardiac model 1 according to the heart behavior data 2, simultaneously with variations in strength of the electrical signal over time according to the electrocardiogram data 3 (step S2). Here the computation unit 12 coordinates the reproduction of heart behavior such that a first shape of the heart at the first time step will be reproduced simultaneously with the first wave of the electrical signal, and such that a second shape of the heart at the second time step will be reproduced simultaneously with the second wave of the electrical signal. More specifically, the computation unit 12 reproduces the first shape at the moment when the reproduced electrical signal reaches a peak (maximum) of the first wave, and reproduces the second shape at the moment when the reproduced electrical signal reaches a peak of the second wave. The computation unit 12 displays the reproduced electrocardiogram and heart behavior on a monitor screen 4, for example.

In operation of the above-described visualization apparatus 10, the computation unit 12 analyzes heart behavior data 2 obtained as result of a simulation and determines a first time step at which the atriums begin to contract. This first time step is distinguished by its number i, where i is an integer equal to or greater than zero. The computation unit 12 also determines a second time step at which the ventricles begin to contract. This second time step is distinguished by its number j, where j is an integer equal to or greater than zero.

The computation unit 12 then reproduces an electrocardiogram and an image depicting the heart's behavior in a synchronized manner. Specifically, the computation unit 12 determines when to reproduce each time step of the heart behavior data 2, on the basis of the electrocardiogram data 3. For example, the i-th time step (i.e., start of atrial contraction) is supposed to be reproduced when the electrical signal exhibits a peak of P wave in the electrocardiogram. That moment is referred to as time ti in FIG. 1. Similarly the j-th time step (i.e., start of ventricular contraction) is supposed to be reproduced when the electrical signal exhibits a peak of R wave in the electrocardiogram. That moment is referred to as time tj in FIG. 1.

In accordance with the reproduction time determined in the way described above, the visualization apparatus 10 dynamically reproduces how the heart changes its shape at each time step, as the electrical signal varies with time in the reproduced electrocardiogram, thus achieving correct synchronization between the electrocardiogram and heart behavior. For example, the electrocardiogram is reproduced as a graph with horizontal and vertical axes respectively representing reproduction time and electrical signal intensity. With the progress of reproduction time, a special mark representing the current position moves along the curved line of the graph so as to indicate the current signal strength being reproduced.

The visualization apparatus 10 displays the synchronized electrocardiogram and heart behavior on a monitor screen 4, thus making it easier for the viewer to understand the relationship between electrical signals seen in the electrocardiogram and actual behavior of the heart. Particularly, the visualization apparatus 10 is designed to adjust the electrocardiogram and heart behavior such that the start of atrial contraction is timed to the peak of P wave, and the start of ventricular contraction is timed to the peak of R wave. This adjustment reflects the delay time from reception of electrical signals by myocardium and consequent contraction of the myocardium, and thus contributes to correct synchronization between the electrocardiogram and heart behavior. More specifically, the atrial myocardium receives an electrical signal when P wave begins. The atriums, however, do not respond immediately, but start to contract some time after the reception of those electrical signals. For realistic reproduction of heart behavior, the visualization apparatus 10 waits for the electrocardiogram to reach the peak of P wave before rendering the contraction of atriums.

The above-described computation unit 12 may be implemented as, for example, functions performed by a processor in the visualization apparatus 10. The storage unit 11 may be implemented as part of the data storage space of memory devices or the like in the visualization apparatus 10.

It is noted that the lines interconnecting the functional blocks in FIG. 1 represent some of their communication paths. The person skilled in the art would appreciate that there may be other communication paths in actual implementations.

(b) Second Embodiment

This section describes a second embodiment, which provides more specific techniques for visualizing the result of behavioral simulation of a patient's heart, precisely in synchronization with his or her electrocardiogram.

FIG. 2 illustrates an exemplary hardware configuration of a computer according to the second embodiment. The illustrated computer 100 includes a processor 101 to control its entire operation. The processor 101 is coupled to a memory 102 and other various devices and interfaces via a bus 109. The processor 101 may be a single processing device or a multiprocessor system including two or more processing devices, such as a central processing unit (CPU), micro processing unit (MPU), or digital signal processor (DSP). It is also possible to implement the processing functions of the processor 101 wholly or partly in an application-specific integrated circuit (ASIC), programmable logic device (PLD), or other electronic circuits, or their combinations.

The memory 102 serves as a primary storage device of the computer 100. Specifically, the memory 102 is used to temporarily store at least some of the operating system (OS) programs and application programs that the processor 101 executes, in addition to other various data objects that it manipulates at runtime. The memory 102 may be, for example, a random access memory (RAM) or other volatile semiconductor memory devices.

Other devices on the bus 109 include a hard disk drive (HDD) 103, a graphics processor 104, an input device interface 105, an optical disc drive 106, a peripheral device interface 107, and a network interface 108. The HDD 103 writes and reads data magnetically on its internal platters. The HDD 103 serves as a secondary storage device in the computer 100 to store program files and data files relating to the operating system and applications. Flash memory and other semiconductor memory devices may also be used as secondary storage devices, in place of or together with the HDD 103.

The graphics processor 104, coupled to a monitor 21, produces video images in accordance with drawing commands from the processor 101 and displays them on a screen of the monitor 21. The monitor 21 may be, for example, a cathode ray tube (CRT) display or a liquid crystal display.

The input device interface 105 is used to connect input devices such as a keyboard 22 and a mouse 23 to the computer 100 and supply signals from these devices to the processor 101. The mouse 23 is a pointing device, which may be replaced with other kinds of pointing devices such as a touchscreen, tablet, touchpad, and trackball.

The optical disc drive 106 reads out data encoded on an optical disc 24, by using laser light or the like. The optical disc 24 is a portable data storage medium, the data recorded on which can be read as a reflection of light or the lack of the same. The optical disc 24 may be a digital versatile disc (DVD), DVD-RAM, compact disc read-only memory (CD-ROM), CD-Recordable (CD-R), or CD-Rewritable (CD-RW), for example.

The peripheral device interface 107 is a communication interface for connecting some peripheral devices to the computer 100. For example, the peripheral device interface 107 may be used to connect a memory device 25 and a memory card reader/writer 26. The memory device 25 is a data storage medium with a capability of communicating with the peripheral device interface 107. The memory card reader/writer 26 is an adapter used to write data to or read data from a memory card 27, which is a data storage medium in the form of a small card. The network interface 108 is connected to a network 20 to exchange data with other computers or network devices (not illustrated).

The above hardware configuration serves as a platform of processing functions to implement the second embodiment. It is noted that the foregoing visualization apparatus 10 of the first embodiment may also be implemented on the same hardware platform discussed in FIG. 2 for the computer 100 of the second embodiment.

The computer 100 provides various processing functions of the second embodiment by executing programs stored in a non-transitory computer-readable storage medium. These processing functions of the computer 100 are encoded in the form of computer programs, which may be stored in a variety of storage media. For example, the computer 100 may store program files in its own HDD 103. The processor 101 loads the memory 102 with at least part of these programs read out of the HDD 103 and executes them on the memory 102. It is also possible to store programs files in an optical disc 24, memory device 25, memory card 27, or the like. The programs stored in a portable storage medium are installed in the HDD 103 under the control of the processor 101, so that they are ready to execute upon request. It may also be possible for the processor 101 to execute program codes read out of a portable storage medium, without installing them in its local storage devices.

Figure 3:
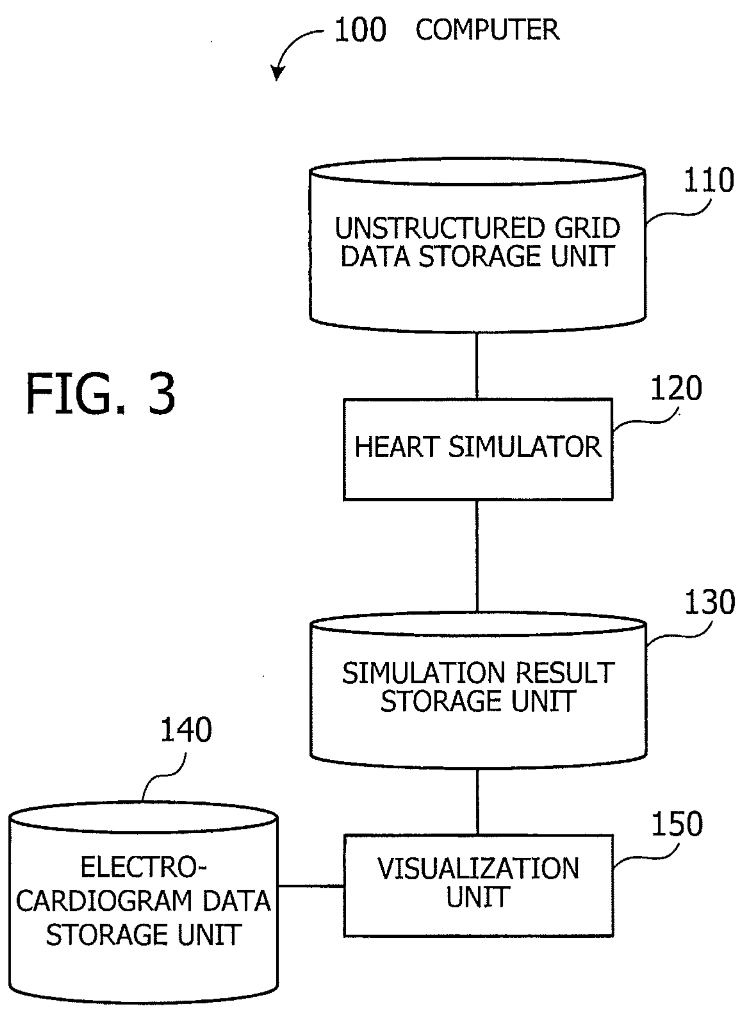
FIG. 3 is a functional block diagram of a computer of the second embodiment.

FIG. 3 is a functional block diagram of a computer of the second embodiment. The illustrated computer 100 includes an unstructured grid data storage unit 110, a heart simulator 120, a simulation result storage unit 130, an electrocardiogram data storage unit 140, and a visualization unit 150.

The unstructured grid data storage unit 110 stores unstructured grid data that describes the shape of a heart in three-dimensional form. For example, unstructured grid data expresses the geometry of a heart as a collection of tetrahedral elements with irregular shapes. More specifically, many nodes are placed in a heart simulation domain, where each four neighboring nodes define a tetrahedron. The heart is thus represented as a collection of many tetrahedrons each serving as an element that portrays myocardial cells. For example, the unstructured grid data storage unit 110 may be implemented as part of storage space of the memory 102 or HDD 103.

The heart simulator 120 mimics the behavior of a heart under test, including its beating motion, on the basis of a given three-dimensional cardiac model. The heart simulator 120 may also simulate coronary circulation (blood flow in the heart). The heart simulator 120 outputs its simulation result to the simulation result storage unit 130. For example, the heart simulator 120 repetitively calculates new node positions of the three-dimensional cardiac model and some relating physical quantities (e.g., blood pressure and amount of blood flow) at each node or cardiac element, while advancing the simulation clock by a predetermined time step size. The node positions and their relating physical quantities at a specific time step are calculated on the basis of those obtained at one or more preceding time steps. The simulation result includes the calculated positions of nodes and new physical quantities at those nodes or elements at each predetermined point on the simulation time axis.

The simulation result storage unit 130 stores data of simulation results discussed above. For example, the simulation result storage unit 130 may be implemented as part of storage space of the memory 102 or HDD 103.

The electrocardiogram data storage unit 140 stores original measurement data of an electrocardiogram of a patient. This data indicates the strength of electrical signals produced in the heart. For example, the electrocardiogram data storage unit 140 may be implemented as part of storage space of the memory 102 or HDD 103.

The visualization unit 150 displays the patient's electrocardiogram and heart behavior on the monitor 21 in a synchronized manner. For example, the simulated heart behavior includes contraction of atriums and ventricles. The visualization unit 150 positions the electrocardiogram in such a way that the peak of P wave will match with the atrial contraction, and the peak of R wave with the ventricular contraction.

The visualization unit 150 is an exemplary implementation of the computation unit 12 discussed previously in FIG. 1 for the first embodiment. The unstructured grid data storage unit 110, simulation result storage unit 130, and electrocardiogram data storage unit 140 are collectively equivalent to the storage unit 11 discussed previously in FIG. 1 for the first embodiment. It is noted that the lines interconnecting the functional blocks in FIG. 3 represent some of their communication paths. The person skilled in the art would appreciate that there may be other communication paths in actual implementations. It is also noted that the functions of each element seen in FIG. 3 may be implemented as program modules executed by a computer.

Figure 4:
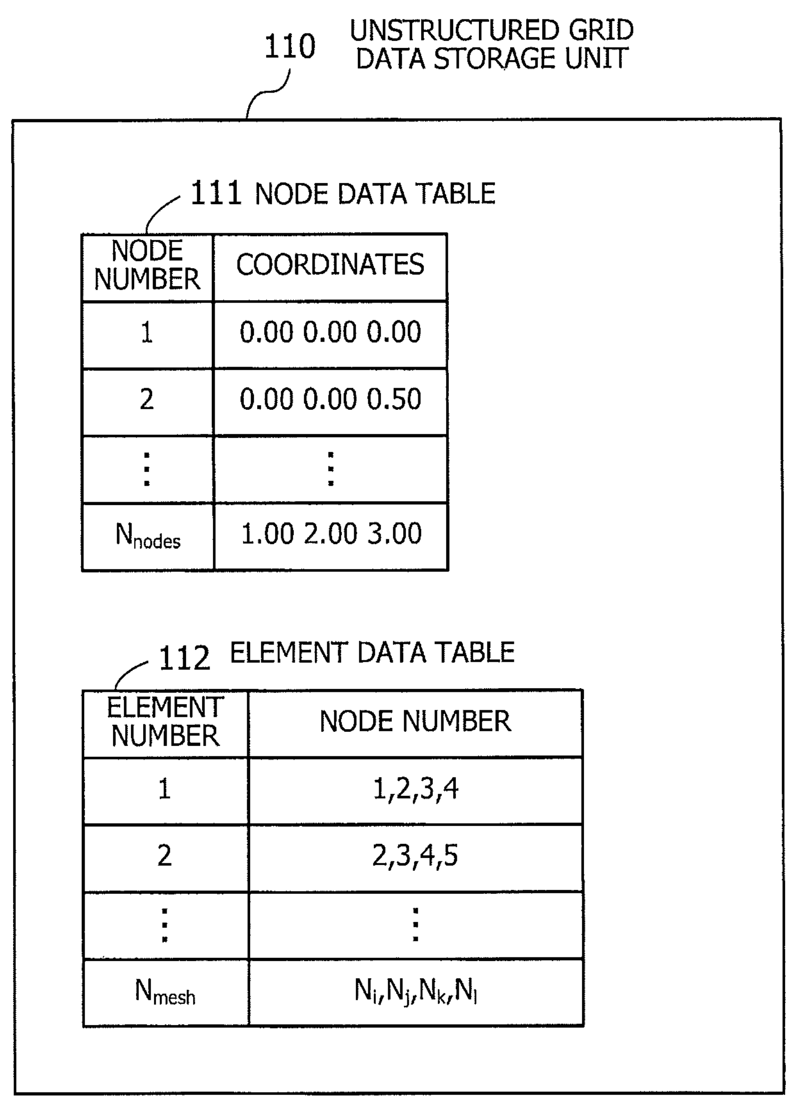
FIG. 4 illustrates an exemplary structure of data stored in an unstructured grid data storage unit.

Referring now to FIG. 4, an exemplary structure of data stored in the unstructured grid data storage unit 110 will be described below. The unstructured grid data storage unit 110 contains, for example, a node data table 111 and an element data table 112, which constitute unstructured grid data. Each entry of the node data table 111 defines a node as a combination of its node number and coordinate position. The node coordinates defined in this node data table 111 indicate the initial position of each node before a simulation is started. During a simulation, these node coordinates in the node data table 111 are changed with the progress of simulated heart beat motion. The element data table 112, on the other hand, describes tetrahedral elements of a cardiac model. Specifically, each tetrahedral element is distinguished by a specific element number, and its four corners are designated by their corresponding node numbers.

Figure 5:
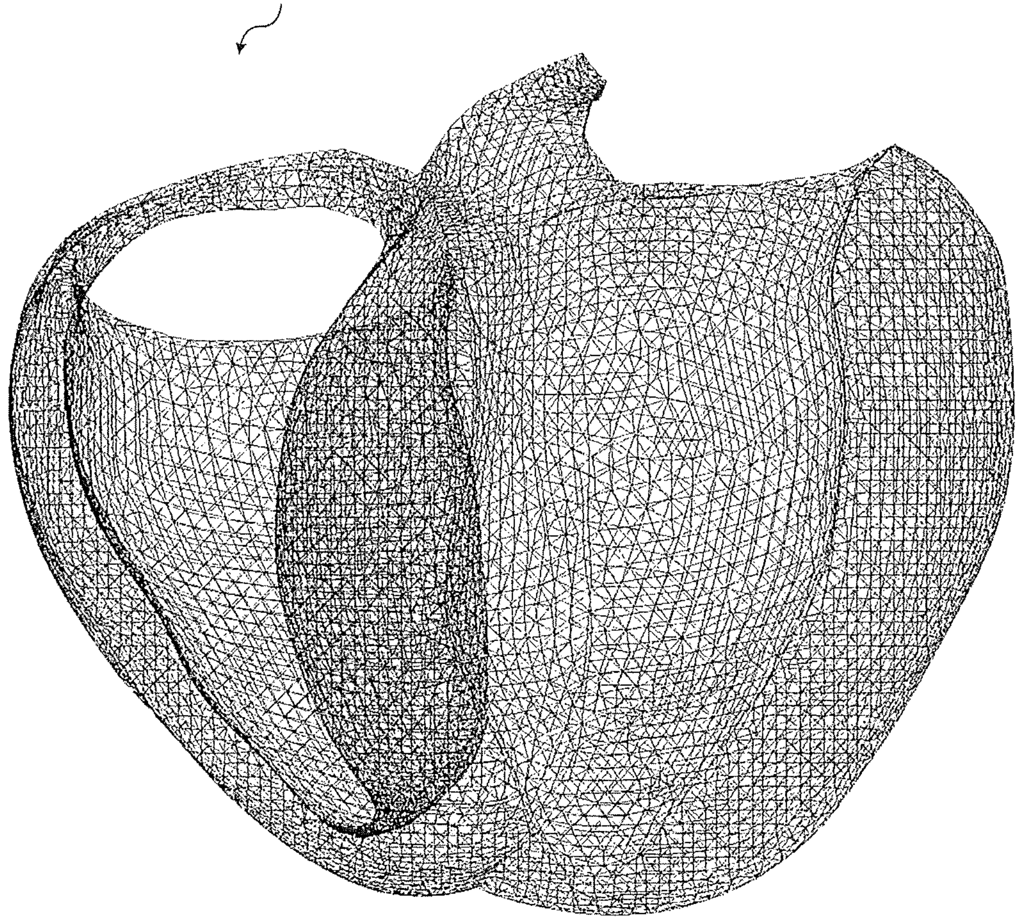
FIG. 5 illustrates an example of a three-dimensional cardiac model.

A three-dimensional cardiac model is produced from the foregoing data in the unstructured grid data storage unit 110 of FIG. 4. FIG. 5 illustrates an example of such a three-dimensional cardiac model. The illustrated three-dimensional cardiac model 31 is made up of a large number of tetrahedral elements. With a given initial condition of electrical signals in this three-dimensional cardiac model 31, the heart simulator 120 computationally reproduces a process of electrical signal conduction (propagation of excitation) in the heart muscle. The three-dimensional cardiac model 31 is also given some other conditions relating to the contraction and relaxation of myocardium, enabling the heart simulator 120 to mimic the heart's mechanical behavior (motion) as well. As the simulation progresses, its outcome is accumulated in the simulation result storage unit 130 in the way described below.

Figure 6:
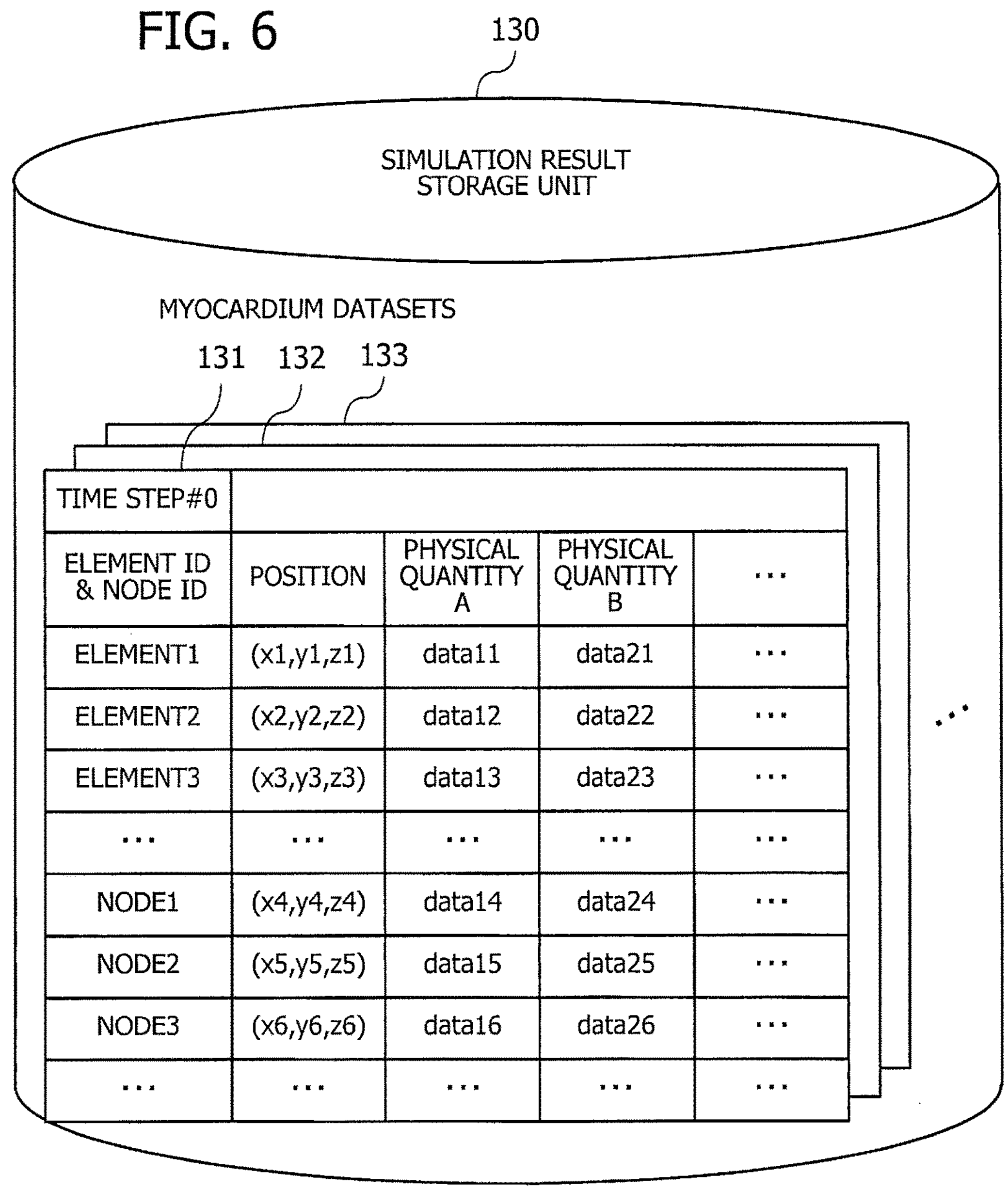
FIG. 6 illustrates an exemplary structure of data stored in a simulation result storage unit.

FIG. 6 illustrates an exemplary structure of data stored in a simulation result storage unit. Each single cycle of computation in the simulation process is referred to as a "simulation time step" or simply "time step." The simulation result storage unit 130 contains a plurality of myocardium datasets 131, 132, 133, obtained at different time steps. These myocardium datasets 131, 132, 133, . . . , given a series of time step indexes, represent how the heart changes its state (including shape) with the progress of simulation time.

More specifically, each record in the myocardium datasets 131, 132, 133, . . . is associated with a particular element or node of the three-dimensional cardiac model and thus includes its element ID or node ID, coordinate position, and various physical quantities. The node positions vary with time, thus representing a varying shape of the heart at each time step. The coordinate position of a tetrahedral element actually means its centroid, or the center of gravity. Each column of physical quantity is populated with data only in the element records, or only in the node records, or in the both.

Figure 7:
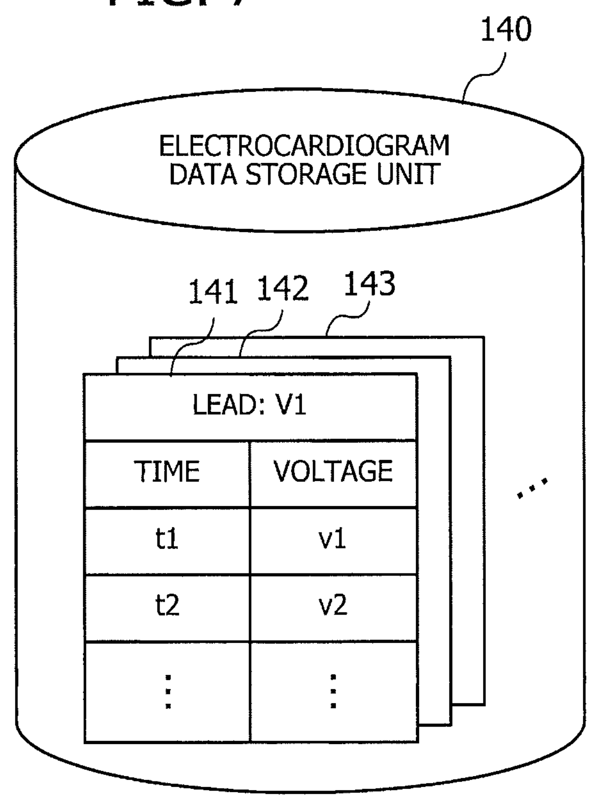
FIG. 7 illustrates an exemplary structure of data stored in an electrocardiogram data storage unit.

Referring now to FIG. 7, the next section describes an exemplary structure of electrocardiogram data stored in the electrocardiogram data storage unit 140. The illustrated electrocardiogram data storage unit 140 stores a plurality of electrocardiogram datasets 141, 142, 143, . . . containing records of voltage observed at different points on the patient's body. In the case of, for example, a twelve-lead electrocardiogram, the electrocardiogram data storage unit 140 stores twelve electrocardiogram datasets corresponding to the twelve leads. Each electrocardiogram dataset 141, 142, 143, . . . is a time-series of voltage values of electrical signals measured with the progress of time relative to the measurement start time.

The above-described electrocardiogram data has been obtained by measuring myocardial voltage of the patient of interest, with a plurality of electrodes attached to his or her body. The measured values of myocardium voltage represent the strength of propagating electrical signals that cause cardiac excitation.

The next section will describe how the excitation propagates over the myocardium and how it is detected as electrical signals.

Figure 8:
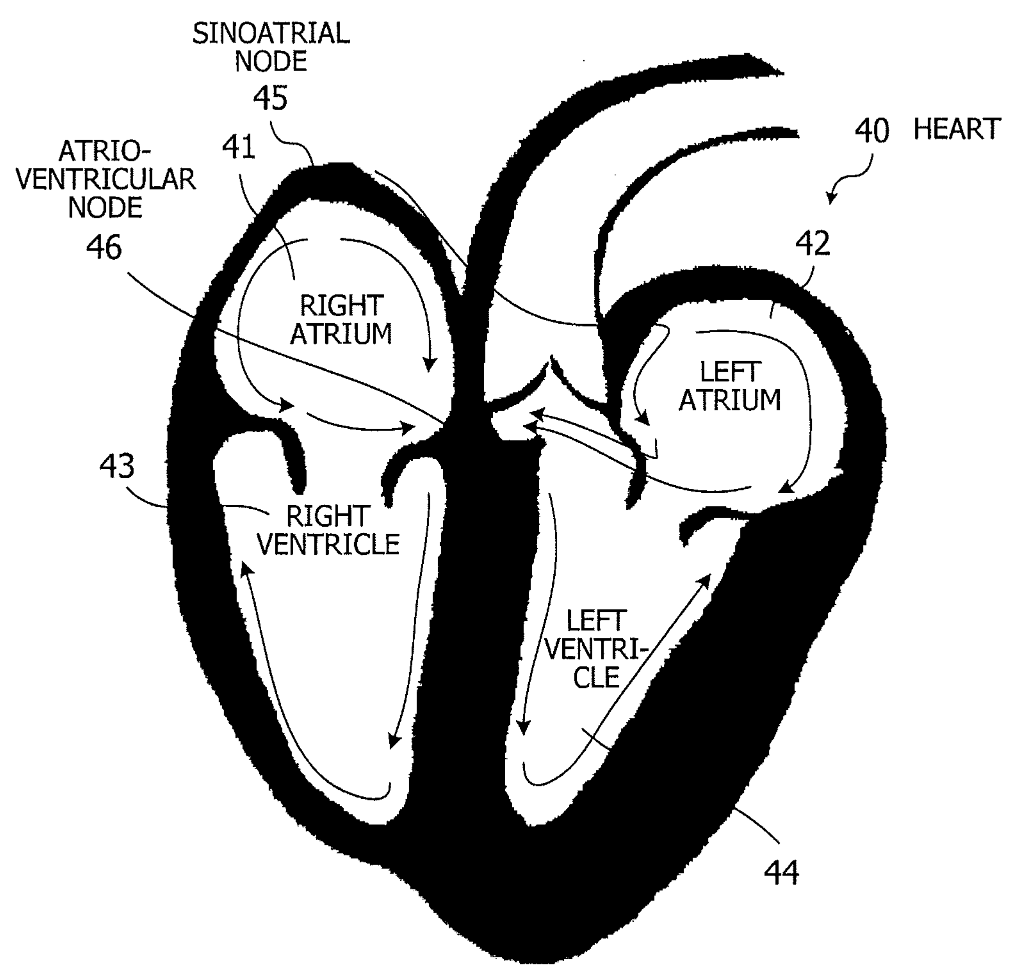
FIG. 8 illustrates an example of propagation of cardiac excitation.

FIG. 8 illustrates an example of propagation of cardiac excitation. The illustrated heart 40 is formed from four chambers called right atrium 41, left atrium 42, right ventricle 43, and left ventricle 44. Each of these heart chambers contracts in accordance with electrical signals that propagate through the heart's stimulus conduction system. Specifically, the stimulus conduction system is made up of a collection of muscle cells specialized for conducting electrical signals that stimulate muscle contraction.

The stimulus conduction system includes a tissue called "sinoatrial node" 45 that serves as the source of electrical signals. The sinoatrial node 45 sits in the right atrium 41 and generates an electrical impulse signal at regular intervals without the need for external stimulation. The generated signal is sent first to the right atrium 41, and to the left atrium 42 as well, and propagates through the atrial muscle before reaching the place called "atrioventricular node" 46. The muscles of the right atrium 41 and left atrium 42 contract in response to the electrical signals that they receive. Then with some delay time after that, the atrioventricular node 46 transfers the electrical signal to the ventricles. The electrical signal then bifurcates to the left and right bundle branches. These signals go down to the bottom of each ventricle and then propagate across the entire ventricular muscle.

Such excitation-causing electrical signals are observed as the voltage potential of myocardium through a process called electrocardiography. The graph representing these recorded voltage variations over time is referred to as an electrocardiogram.

Figure 9:
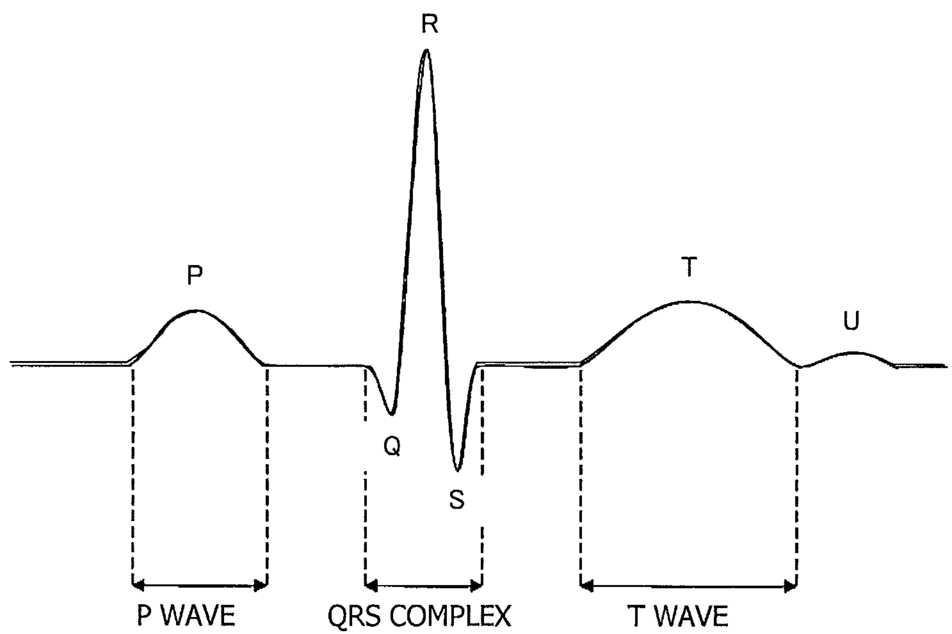
FIG. 9 illustrates an example of an electrocardiogram.

FIG. 9 illustrates an example of an electrocardiogram. A healthy heart exhibits six waves named P, Q, R, S, T, and U waves in its electrocardiogram. Q, R, and S waves occur back-to-back (i.e., without interruption) and are collectively referred to as a QRS complex. P wave represents depolarization (excitation) of the atriums. That is, P wave is the first upward (i.e., positive) wave that comes after the electrical signal begins to propagate in a heart beat cycle. The subsequent QRS complex represents depolarization (excitation) of the ventricles, which begins with a downward (i.e., negative) Q wave and continues to an upward R wave and then to a downward S wave.

Figure 10:
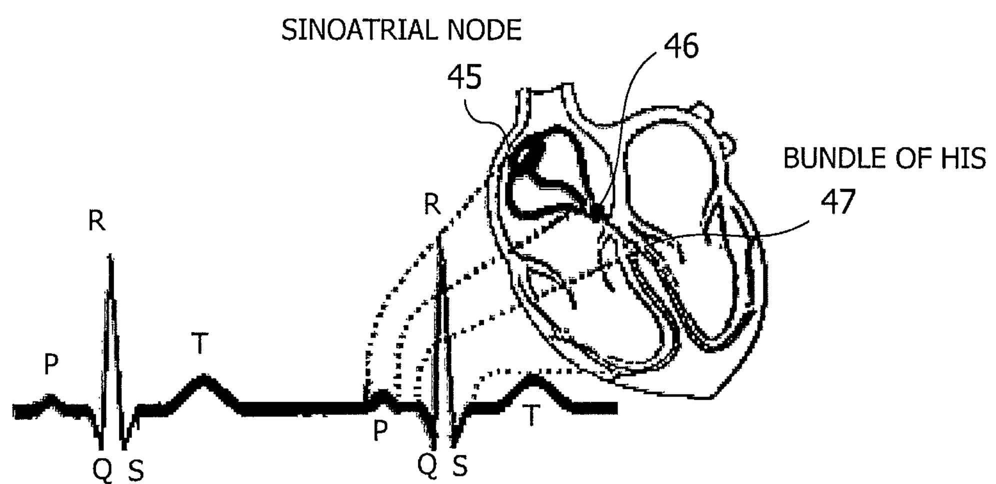
FIG. 10 illustrates how an electrocardiogram relates to propagation of cardiac excitation.

FIG. 10 illustrates how an electrocardiogram relates to propagation of cardiac excitation. Specifically, the sinoatrial node 45 generates an electrical signal, initiating P wave. This P wave disappears when the electrical signal reaches the atrioventricular node 46. The electrical signal further propagates from the atrioventricular node 46 through the bundle of His 47 and bifurcates into the left and right bundle branches, causing a QRS complex to begin. The QRS complex is finished when the bifurcated electrical signals arrive at the extreme ends of those two bundle branches within the ventricular myocardium.

Figure 11:
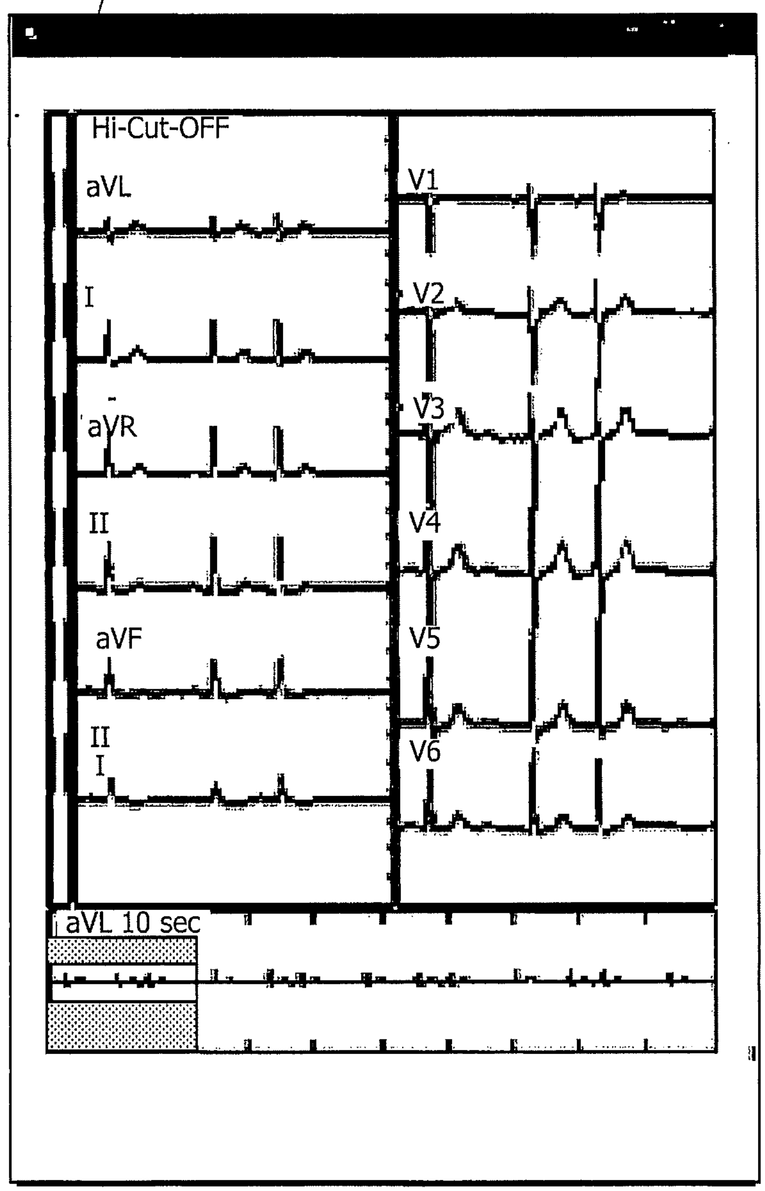
FIG. 11 illustrates an example of a twelve-lead electrocardiogram.

Most electrocardiograms are obtained as twelve leads, meaning that twelve different views of a heart are captured at a time. FIG. 11 illustrates an example of a twelve-lead electrocardiogram. The illustrated twelve-lead electrocardiogram 51 actually includes twelve different waveforms, or leads. Many leads have R waves larger than their subsequent S waves (negative), while some may exhibit S waves larger than R waves. There may even be a missing wave in some of those leads. Electrocardiograms contain some amount of noise introduced during the measurement process, which may be visible in their waveforms.

The computer 100 of the second embodiment displays such an electrocardiogram together with a picture visualizing simulated behavior of the heart in question. This feature of the computer 100 permits the user to understand how the heart behaves in response to electrical signals seen in the electrocardiogram.

The patient's electrocardiogram is used to determine the values of parameters for a behavioral simulation of his or her heart. With such parameters based on electrocardiogram data, the simulation result will reflect the condition of the patient's cardiac excitation system. Suppose, for example, the patient in question has a symptom of cardiac arrhythmia. The use of his electrocardiogram data for simulation makes it possible to reproduce the heart's behavior under the arrhythmic condition.

The visualization unit 150 makes some timing adjustment to synchronize the heart actions with the given electrocardiogram when reproducing them on a monitor screen. Specifically, P wave in the electrocardiogram is timed to atrial contraction caused by an electrical signal from the sinoatrial node 45, and R wave is timed to ventricular contraction caused by an electrical signal from the atrioventricular node 46. In other words, the visualization unit 150 renders the reproduced heart behavior so as to make the atriums begin to contract at the peak point of P wave, as well as to make the ventricles begin to contract at the peak point of R wave.

Figure 12:
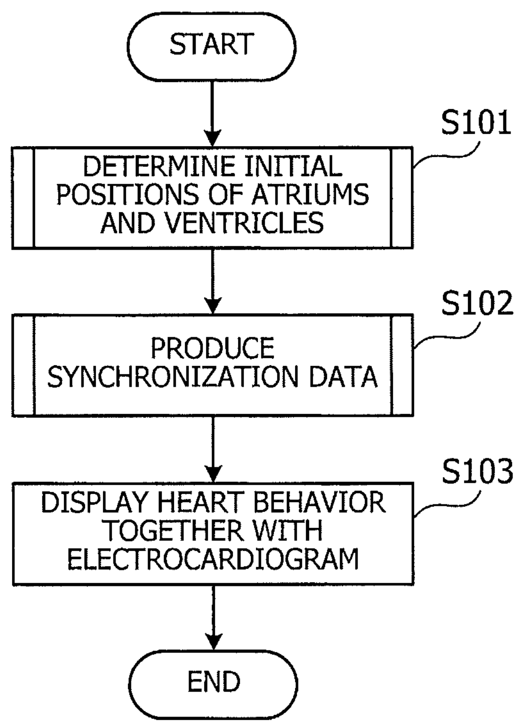
FIG. 12 is a flowchart of a visualization process.

The following description will now explain how the visualization unit 150 reproduces heart behavior in a three-dimensional model in synchronization with a corresponding electrocardiogram. FIG. 12 is a flowchart of a visualization process.

(Step S101) The visualization unit 150 determines initial positions of atriums and ventricles. For example, two points in the atriums or ventricles are selected such that they are as distant as possible, assuming that it is before a heart beat begins. A displacement of atriums from their initial positions will be interpreted as a start of atrial contraction. Similarly, a displacement of ventricles from their initial positions will be interpreted as a start of ventricular contraction. Details of this step S101 will be discussed later with reference to FIG. 13.

(Step S102) The visualization unit 150 produces synchronization data that specifies when to reproduce heart behavior of each time step. Details of this processing will be discussed later with reference to FIG. 17.

(Step S103) The visualization unit 150 reproduces behavior of the heart in its three-dimensional model, and the visualization unit 150 displays it on the monitor 21 in synchronization with an electrocardiogram.

Figure 13:
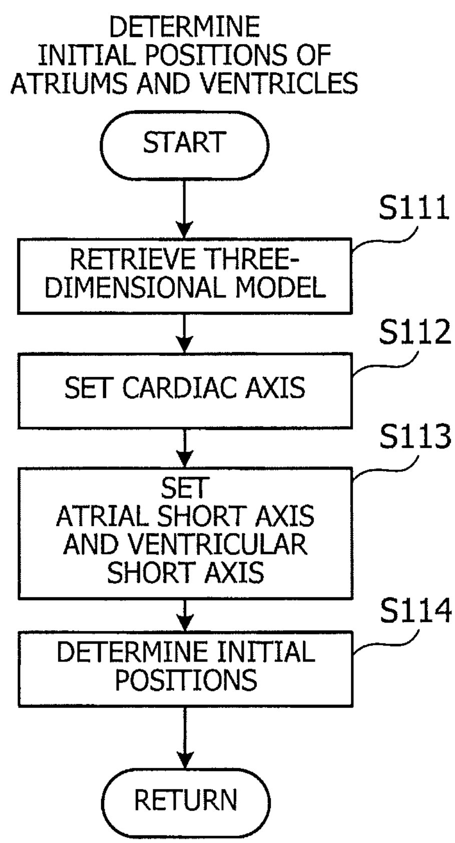
FIG. 13 is a flowchart illustrating a procedure of determining initial positions of atriums and ventricles.

The description will now provide details of how to determine the initial positions of atriums and ventricles. FIG. 13 is a flowchart illustrating a procedure of determining initial positions of atriums and ventricles.

(Step S111) The visualization unit 150 retrieves data of a three-dimensional cardiac model 31 from the unstructured grid data storage unit 110.

(Step S112) The visualization unit 150 sets a cardiac axis (long axis of the heart) in the three-dimensional cardiac model 31. The long axis runs through the heart in its vertical direction.

(Step S113) The visualization unit 150 sets an atrial short axis and a ventricular short axis in three-dimensional cardiac model 31. The atrial short axis refers to a lateral axis of atriums that is perpendicular to the long axis of the heart. The ventricular short axis refers to a lateral axis of ventricles that is perpendicular to the long axis of the heart.

(Step S114) The visualization unit 150 calculates the coordinates of points at which the atrial short axis intersects with free walls of myocardium and determines these intersectional coordinates as the initial positions of atriums. Similarly, the visualization unit 150 calculates the coordinates of points at which the ventricular short axis intersects with free walls of myocardium and determines these intersectional coordinates as the initial positions of ventricles.

A specific example of initial position setup will now be described below with reference to FIGS. 14 to 16. The process starts with setting a long axis of the heart in its three-dimensional cardiac model. It is assumed here that the heart is in the condition before a heart beat begins. The visualization unit 150 sets a long axis through the bottommost portion of a ventricular cavity.

Figure 14:
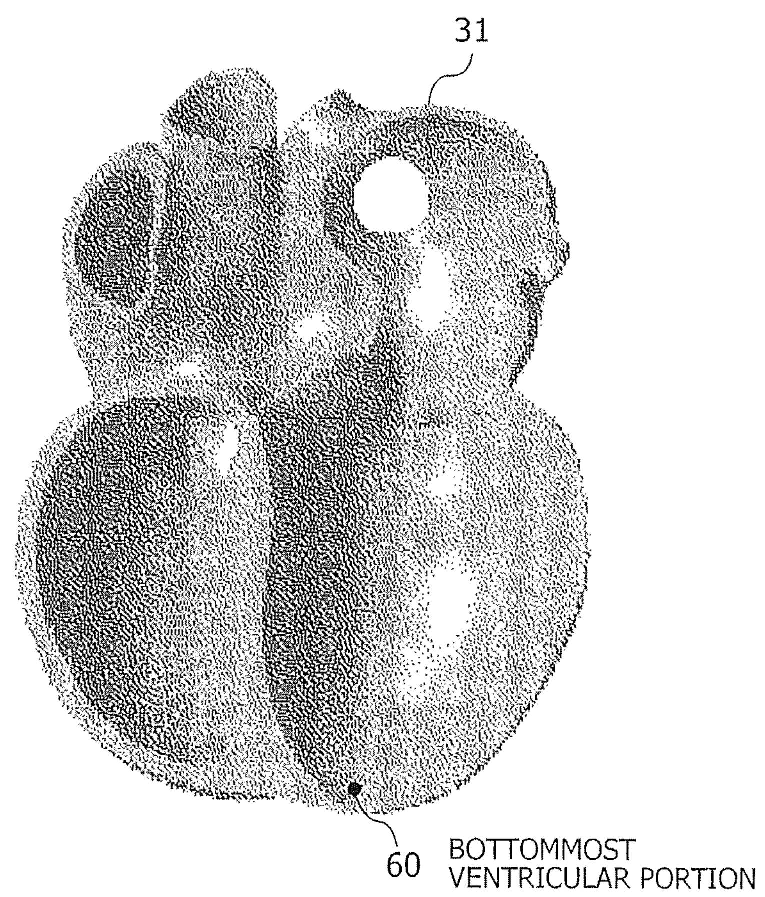
FIG. 14 illustrates the bottommost portion of a ventricular cavity.

FIG. 14 illustrates the bottommost portion of a ventricular cavity. The long axis is defined as a straight line passing through the illustrated bottommost ventricular portion 60 in the three-dimensional cardiac model 31.

Figure 15:
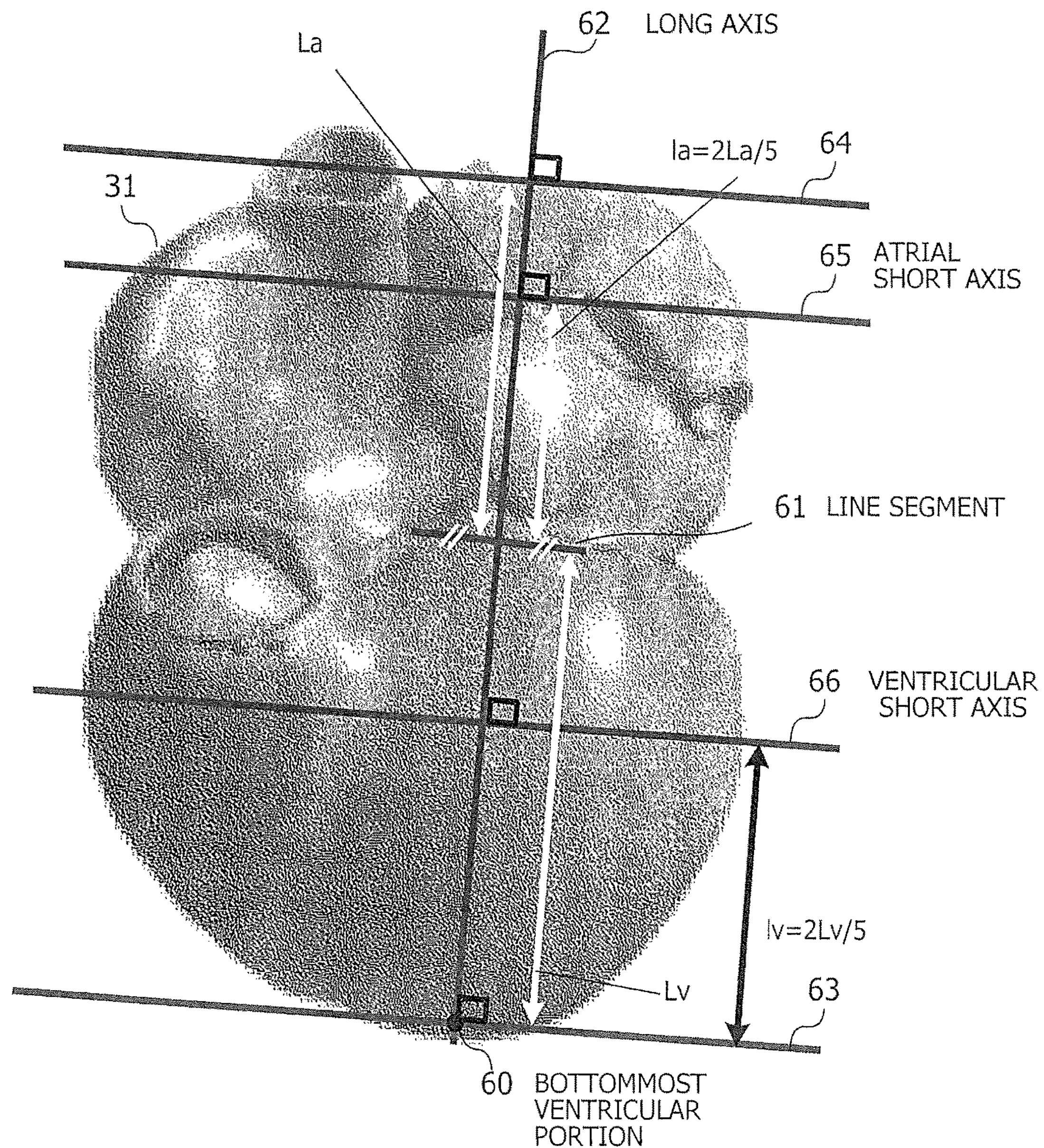
FIG. 15 illustrates an example of long and short axes.
Figure 16:
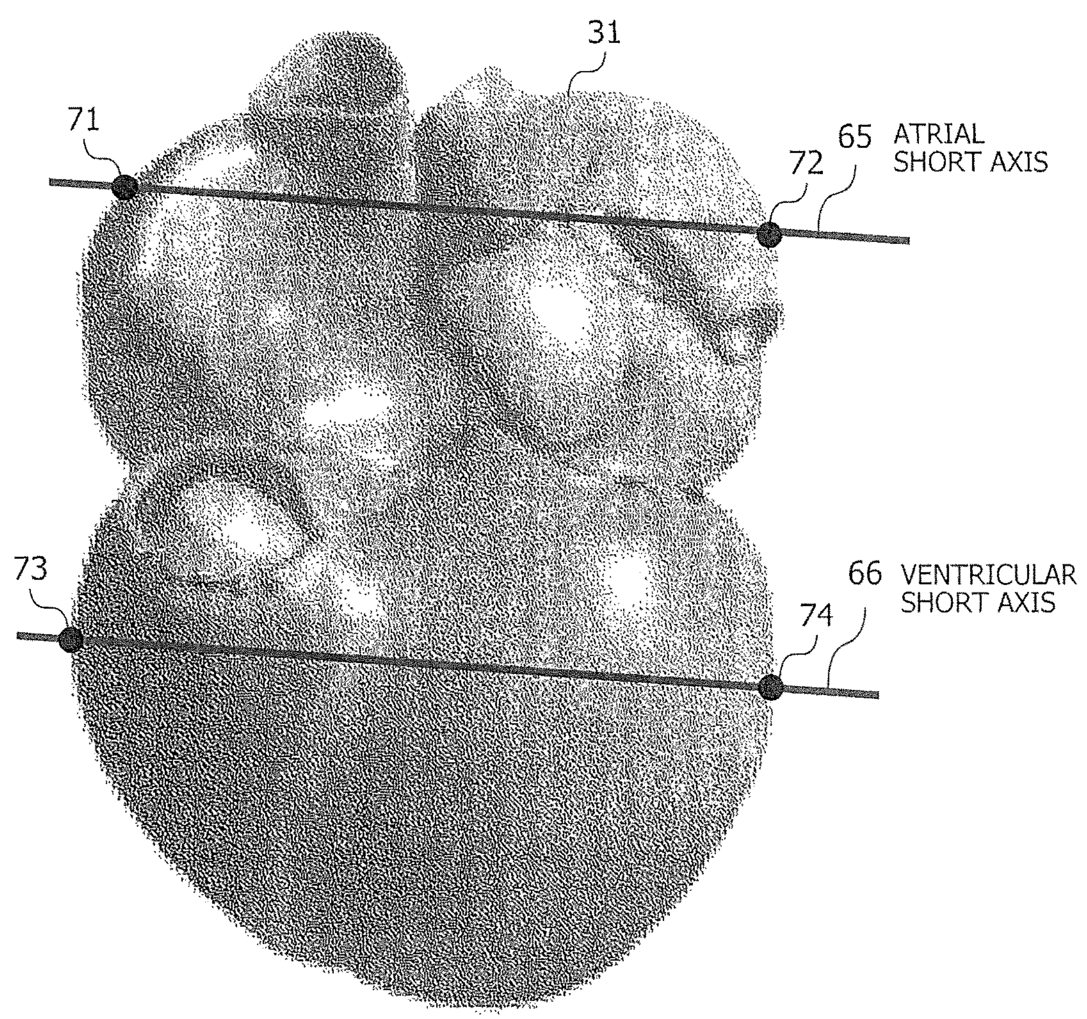
FIG. 16 illustrates initial positions.

FIG. 15 illustrates an example of long and short axes. The visualization unit 150 draws a line segment 61 between the center of the aorta valve and that of the mitral valve in the three-dimensional cardiac model 31. The visualization unit 150 then determines the midpoint of this line segment 61 and draws a straight line that goes through the midpoint and the above-noted bottommost ventricular portion 60, thereby determining a long axis 62 as seen in FIG. 15.

The visualization unit 150 then produces two straight lines 63 and 64 perpendicular to the long axis 62. One straight line 63 passes through the bottommost ventricular portion 60. The other straight line 64 meets the long axis 62 at the topmost point of the heart. Let La be the distance between the line segment 61 and the latter straight line 64, and Lv be the distance between the line segment 61 and the former straight line 63. The visualization unit 150 now draws a straight line that is perpendicular to the long axis 62 and apart from the line segment 61 at a distance of la being equal to two fifths of La. This straight line will be an atrial short axis 65 of the heart. The visualization unit 150 draws another straight line that is perpendicular to the long axis 62 and apart from the straight line 63 at a distance of lv being equal to two fifths of Lv. This straight line will be a ventricular short axis 66 of the heart.

The visualization unit 150 now determines at which points the atrial short axis 65 meets free walls (cardiac walls other than the septum) of the atriums. These points are initial positions of the atriums. Similarly, the visualization unit 150 determines at which points the ventricular short axis 66 meets free walls of the ventricles, and sets these points as initial positions of the ventricles. FIG. 16 illustrates such initial positions. Specifically, two initial positions 71 and 72 are seen on the atrial short axis 65 in the three-dimensional cardiac model 31, and another two initial positions 73 and 74 are seen on the ventricular short axis 66.

The above-described procedure determines initial positions of atriums and ventricles. Based on those initial positions, the visualization unit 150 produces synchronization data as a preparation for reproduction of heart behavior recorded in myocardium datasets 131, 132, 133, and so on. For example, the visualization unit 150 seeks a time point at which the atrial free walls move from their initial positions 71 and 72 and maps that time point to the peak of P wave seen in the electrocardiogram. The visualization unit 150 also seeks another time point at which the ventricular free walls move from their initial positions 73 and 74 and maps that time point to the peak of R wave seen in the electrocardiogram.

The visualization unit 150 further maps a single heart beat cycle in the myocardium datasets to that in the electrocardiogram. For example, a heart beat cycle is defined as a period from the peak of one P wave to that of the next P wave. As an alternative, a heart beat cycle may refer to a period between the rising edges of two P waves in the case where the first simulation time step corresponds to the time point when the sinoatrial node 45 starts to output an electrical signal. As another alternative, a heart beat cycle may start at a change in the ventricles from relaxation to contraction and end at another such change. Such a change from relaxation to contraction of ventricles occurs after R wave appears in the QRS period (i.e., from the beginning of Q wave to the end of S wave).

Figure 17:
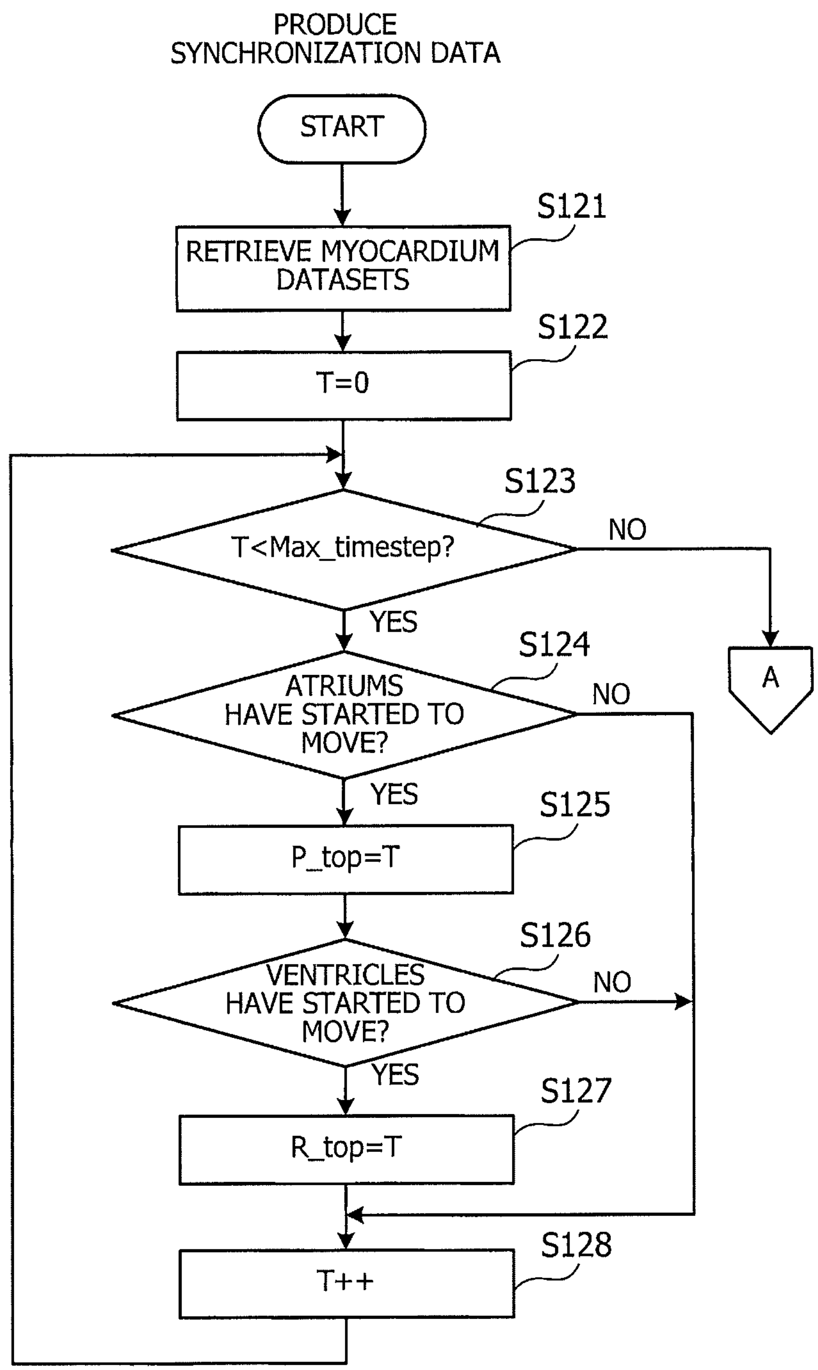

The visualization unit 150 now produces synchronization data in the way described below. The synchronization data enables the visualization unit 150 to determine when to reproduce each time step of simulated heart behavior, while ensuring its synchronization with an associated electrocardiogram. FIGS. 17 and 18 are first and second halves of a flowchart illustrating a procedure of producing synchronization data.

(Step S121) The visualization unit 150 retrieves a myocardium dataset 131, 132, 133, . . . of each time step from the simulation result storage unit 130.

(Step S122) The visualization unit 150 initializes a variable T to zero, where T indicates the current time step number.

(Step S123) The visualization unit 150 determines whether variable T is smaller than Max_timestep, or the total number of time steps constituting a single heart beat cycle. If T is smaller than Max_timestep, the process advances to step S124. Otherwise, the process branches to step S131 in FIG. 18.

(Step S124) Variable T has not reached the end of the heart beat cycle. The visualization unit 150 thus checks the cardiac shape of time step T to determine whether the atrial myocardium has started to move from its initial position. For example, the visualization unit 150 watches the current positions of some pieces of atrial myocardium while variable P_top contains no values. When any movement from their initial positions is found at time step T, the visualization unit 150 determines that the atrial myocardium started to move at that time step T, which means that the atriums have started to contract. Upon detection of such a movement, the process advances to step S125. The process skips to step S128 when there is no such movement as of time step T, or the atriums have already started to move.

(Step S125) The visualization unit 150 assigns the current value of T to variable P_top to record the time step at which the atriums started contraction.

(Step S126) The visualization unit 150 checks the cardiac shape of time step T to determine whether the ventricular myocardium has started to move from its initial position. For example, the visualization unit 150 watches the current positions of some pieces of ventricular myocardium while variable R_top contains no values. When any movement from their initial positions is found at time step T, the visualization unit 150 determines that the ventricular myocardium started to move at that time step T, which means that the ventricles have started to contract. Upon detection of such a movement, the process advances to step S127. The process skips to step S128 when there is no such movement as of time step T, or the ventricles have already started to move.

(Step S127) The visualization unit 150 assigns the current value of T to variable R_top to record the time step at which the ventricles started contraction.

(Step S128) The visualization unit 150 increments variable T by one and makes the process go back to step S123.

The above-described processing steps of FIG. 17 cause two variables P_top and R_top to gain their values respectively indicating at which time steps the atriums and ventricles started contraction. The visualization unit 150 then determines when to render the cardiac shape of each subsequent time step as defined in the myocardium datasets.

FIG. 18 is the second half of the flowchart illustrating a procedure of generating synchronization data.

(Step S131) The visualization unit 150 retrieves electrocardiogram datasets 141, 142, 143, . . . from the electrocardiogram data storage unit 140.

(Step S132) The visualization unit 150 initializes variable T to zero.

(Step S133) The visualization unit 150 calculates a first time interval Δt1 of each time step of heart behavior that is supposed to be reproduced in the period from the beginning of electrical signal output to the peak of P wave in the electrocardiogram. Suppose, for example, that the myocardium datasets include n1 time steps between the beginning of a heart beat cycle and the time step P_top. Also suppose that the electrocardiogram gives a time length of t1 between the beginning of electrical signal output and the peak of P wave. The visualization unit 150 obtains Δt1 by dividing t1 by n1.

(Step S134) The visualization unit 150 determines whether variable T is smaller than P_top. If T is smaller than P_top, the process advances to step S135. Otherwise, the process proceeds to step S137.

(Step S135) As will be illustrated later, the synchronization data specifies reproduction time of each time step of heart behavior. At this step S135, the visualization unit 150 determines reproduction time for time step T such that the cardiac shape of time step T will be rendered Δt1 after that of time step (T−1). It is noted that time step 0 is supposed to be reproduced simultaneously with the start of a single heart beat cycle in the electrocardiogram.

(Step S136) The visualization unit 150 increments variable T by one and moves the process back to step S134.

(Step S137) The visualization unit 150 calculates a second time interval Δt2 of each time step of heart behavior that is supposed to be reproduced in the period from the peak of P wave to the peak of R wave in the electrocardiogram. Suppose, for example, that the myocardium datasets include n2 time steps between two time steps P_top and R_top. Also suppose that the electrocardiogram gives a time length of t2 between the peak of P wave and the peak of R wave. The visualization unit 150 obtains Δt2 by dividing t2 by n2.

(Step S138) The visualization unit 150 determines whether variable T is smaller than R_top. If T is smaller than R_top, the process advances to step S139. Otherwise, the process proceeds to step S141.

(Step S139) The visualization unit 150 determines reproduction time for time step T such that the cardiac shape of time step T will be rendered Δt2 after that of time step (T−1).

(Step S140) The visualization unit 150 increments variable T by one and makes the process go back to step S138.

(Step S141) The visualization unit 150 calculates a third time interval Δt3 of each time step of heart behavior that is supposed to be reproduced in the period from the peak of R wave to the end of the heart beat cycle in the electrocardiogram. Suppose, for example, that the myocardium datasets include n3 time steps between time step R_top and the last time step of the heart beat cycle. Also suppose that the electrocardiogram gives a time length of t3 between the peak of R wave and the end of the heart beat cycle. The visualization unit 150 obtains Δt3 by dividing t3 by n3.

(Step S142) The visualization unit 150 determines whether variable T is smaller than Max_timestep, or the number of time steps constituting the heart beat cycle. If T is smaller than Max_timestep, the process advances to step S143. Otherwise, the visualization unit 150 exits from the present process of FIG. 18.

(Step S143) The visualization unit 150 determines reproduction time for time step T such that the cardiac shape of time step T will be rendered Δt3 after that of time step (T−1).

(Step S144) The visualization unit 150 increments variable T by one and makes the process go back to step S142.

The above-described processing steps enable the visualization unit 150 to produce synchronization data that specifies when to reproduce the cardiac shape of each time step.

Figure 19:
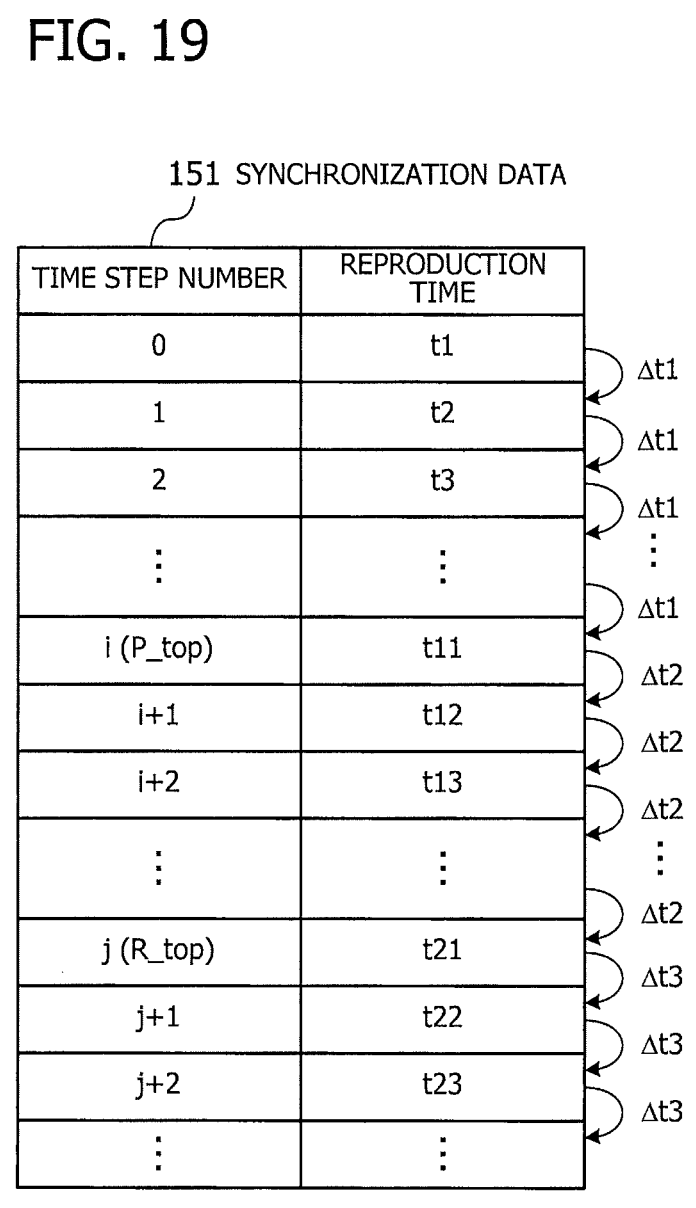

FIG. 19 illustrates an example of synchronization data. The illustrated synchronization data 151 contains time code values associated with different time step numbers. These values are labeled "reproduction time" and each indicate when the cardiac shape of the associated time step is to be rendered, in terms of the elapsed time since the beginning of a heart beat cycle in the electrocardiogram. This synchronization data 151 is located in, for example, a storage space of the memory 102 that the visualization unit 150 manages.

It is noted that the synchronization data may be implemented in other forms than the table illustrated in the example of FIG. 19. For example, the synchronization data may be contained in an array of time code values indexed by the time step number.

It is also noted that one heart beat cycle period may be divided differently from the foregoing example of FIGS. 18 and 19, which has illustrated three sections demarcated by the peaks of P and R waves. For example, the visualization unit 150 may be configured to calculate the interval of each time step in a unified period from the peak of R wave in one heart beat cycle to the peak of P wave in the next cycle.

The above description has discussed how the visualization unit 150 produces synchronization data 151. This synchronization data 151 is used to reproduce the heart behavior on a monitor screen so that the user can see it in synchronization with an electrocardiogram.

Figure 20:
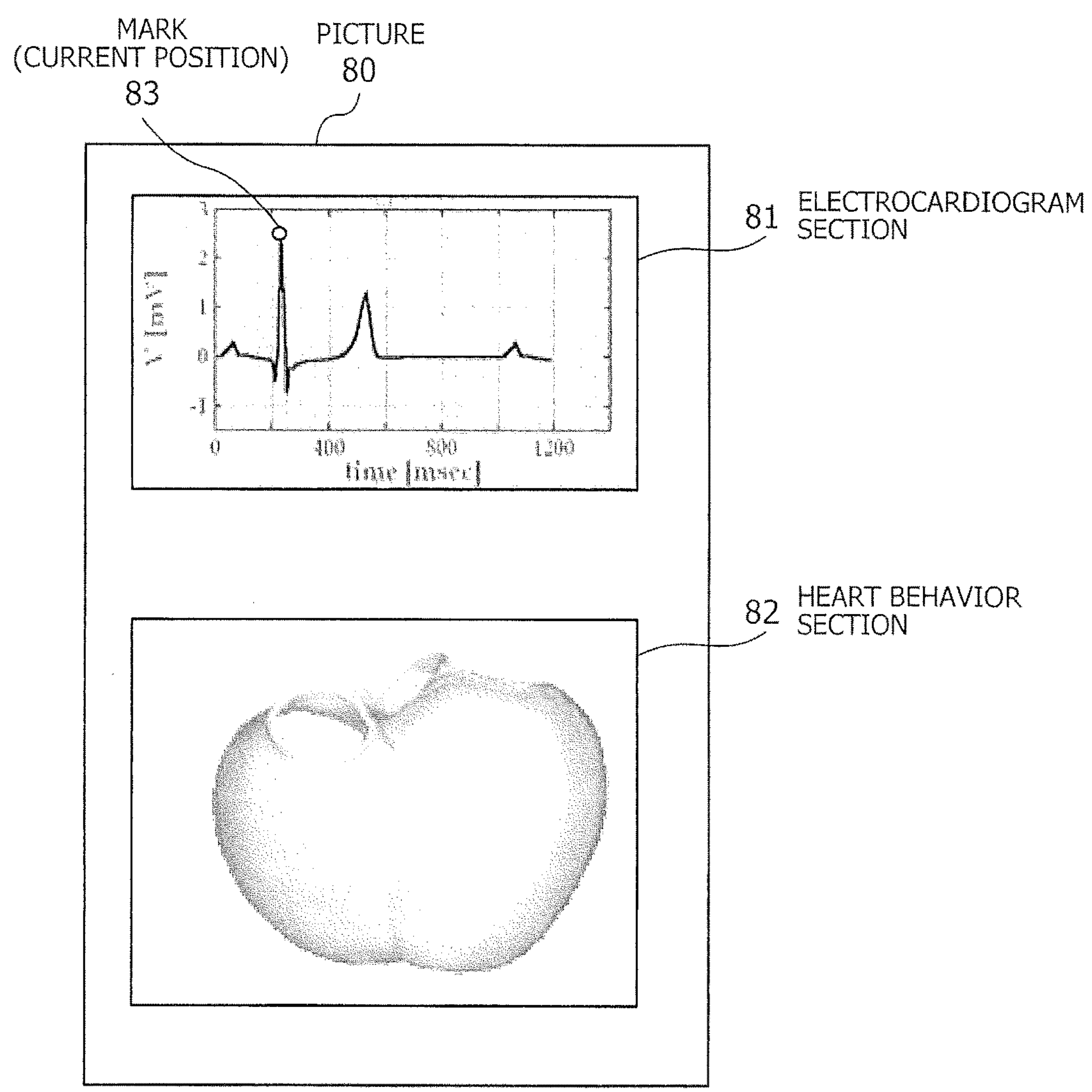
FIG. 20 illustrates an example of a picture that reproduces heart behavior together with an electrocardiogram.

FIG. 20 illustrates an example of a picture that reproduces heart behavior together with an electrocardiogram. The illustrated picture 80 is formed from an electrocardiogram section 81 and a heart behavior section 82. The electrocardiogram section 81 displays an electrocardiogram reproduced from electrocardiogram data, with a mark 83 indicating which time point is being reproduced. For example, the mark 83 moves from left to right along the waveform indicating voltage strength in the electrocardiogram, according to the progress of cardiac image reproduction.

The heart behavior section 82 depicts the behavior of the heart in the form of a three-dimensional model by deforming its shape in accordance with a series of myocardium datasets 131, 132, 133, and so on. That is, the three-dimensional model seen in the heart behavior section 82 has a shape reproduced from a myocardium dataset that corresponds to the reproduction time indicated by the mark 83 in the electrocardiogram section 81. The three-dimensional model is updated with its new myocardium dataset as the mark 83 moves with time, so that the behavior of the heart will be presented in an animated way.

Figure 21:
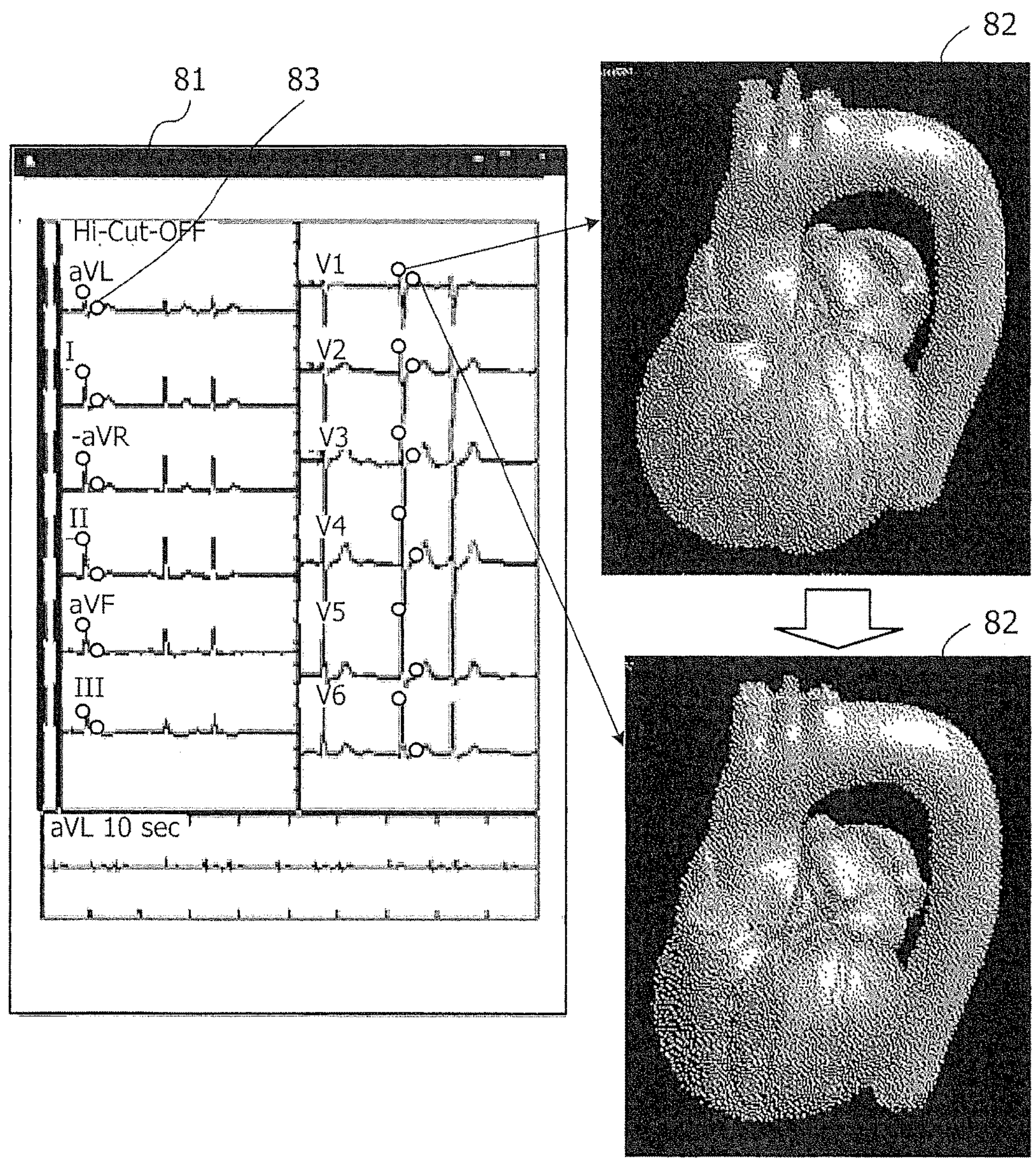
FIG. 21 illustrates an exemplary screenshot of a twelve-lead electrocardiogram.

While the above example of FIG. 20 depicts only one lead, the electrocardiogram section 81 may optionally display all waveforms of twelve leads. FIG. 21 illustrates an exemplary screenshot of a twelve-lead electrocardiogram. The illustrated electrocardiogram section 81 presents all waveforms of a twelve-lead electrocardiogram, each having a mark 83 indicating the current time point in the waveforms. Seen in the heart behavior section 82 is a reproduced image of the heart at the current time point (reproduction time) indicated by the mark 83, relative to the beginning of the electrocardiogram. The cardiac image in the heart behavior section 82 changes as the mark 83 moves rightward.

Figure 22:
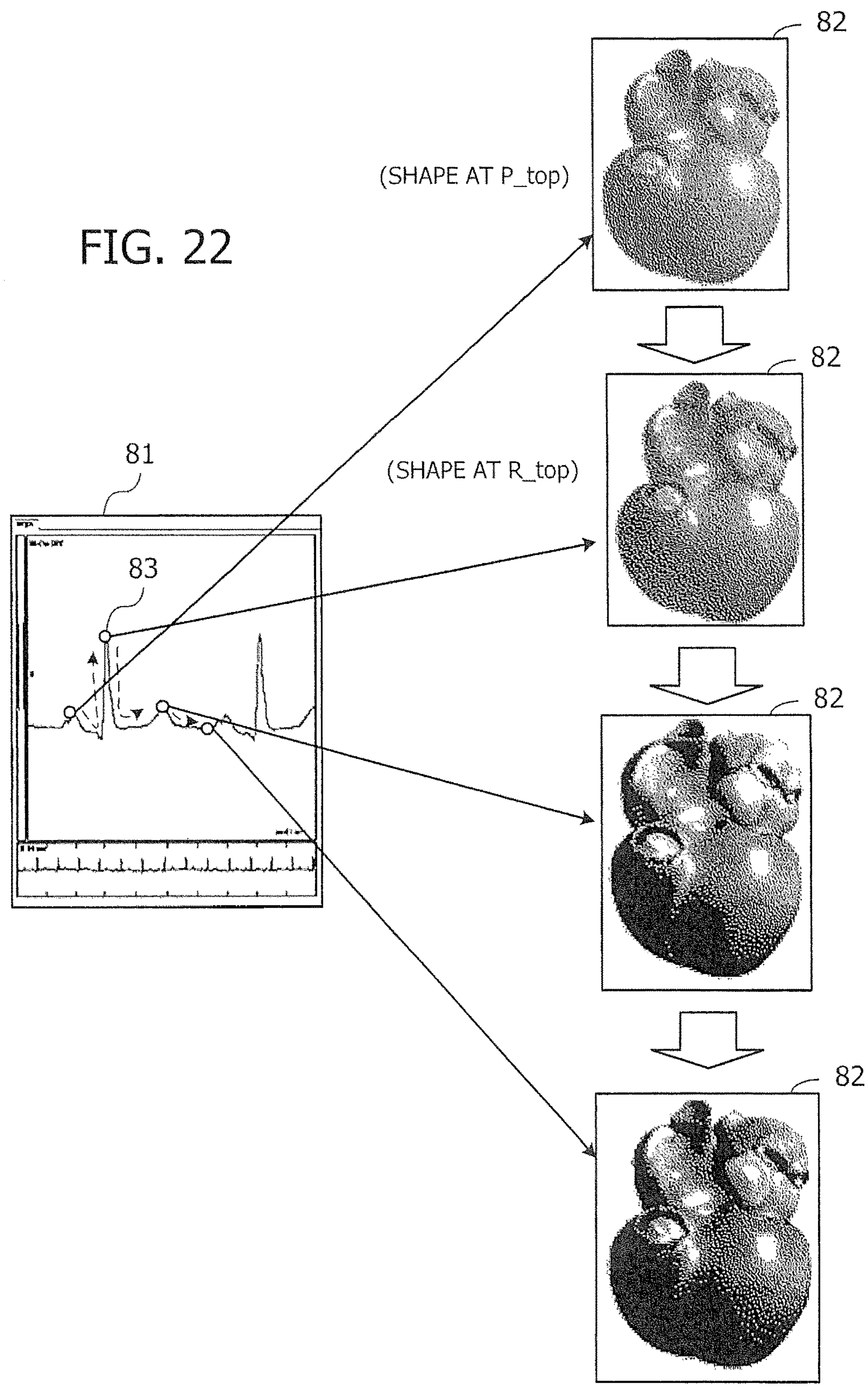
FIG. 22 illustrates how the heart changes its shape with the progress of reproduction time.

FIG. 22 illustrates how the heart changes its shape with the progress of reproduction time. The illustrated mark 83 moves rightward along the waveform of electrocardiogram in the electrocardiogram section 81 with the passage of reproduction time. The heart behavior section 82, on the other hand, contains an image of the heart at a time point corresponding to the current voltage indicated by the mark 83 in the electrocardiogram. For example, when the mark 83 is at the peak of P wave, the heart behavior section 82 displays the shape of the heart at time step P_top. When the mark 83 is at the peak of R wave, the heart behavior section 82 displays the shape of the heart at time step R_top.

Figure 23:
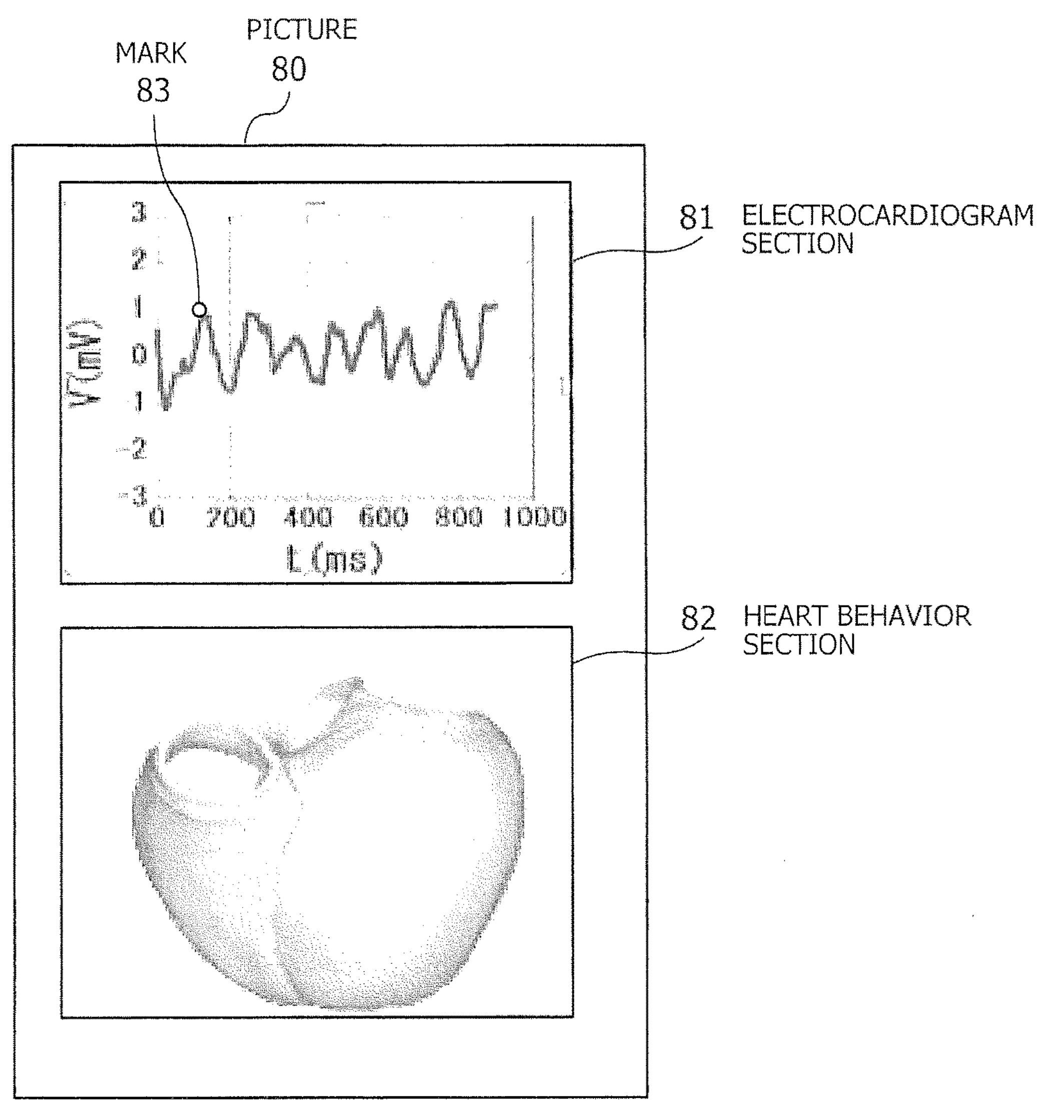
FIG. 23 illustrates an exemplary screenshot that depicts heart behavior together with an electrocardiogram in the case of arrhythmia.

The proposed techniques of the second embodiment are not limited to the visualization of normal heart behavior, but may also be applied to the case of arrhythmia. That is, it is possible to depict an arrhythmic heart beat in synchronization with an electrocardiogram of a patient experiencing arrhythmia. FIG. 23 illustrates an exemplary screenshot that depicts heart behavior together with an electrocardiogram in the case of arrhythmia. More particularly, FIG. 23 illustrates the case of tachyarrhythmia. This means that the patient's electrocardiogram contains more frequent waves than normal persons', which may be observed in the heart behavior section 82 as unnatural creases on the heart surface.

As can be seen from the above examples, an animated image of a patient's heart is displayed in synchronization with his or her electrocardiogram, thus making it easier for the user to understand how the heart actually behaves when a particular pattern of electrical signals appears in the electrocardiogram. In this way, the proposed techniques contribute to more precise diagnosis of the patient's medical condition.

In one aspect of the embodiments described above, the proposed techniques enable synchronized reproduction of a measured electrocardiogram and a simulated behavior of the heart under diagnosis.

All examples and conditional language provided herein are intended for the pedagogical purposes of aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although one or more embodiments of the present invention have been described in detail, it should be understood that various changes, substitutions, and alterations could be made hereto without departing from the spirit and scope of the invention.

What is claimed is:

1. A visualization apparatus comprising:

a memory configured to store a three-dimensional model of a heart of a patient, heart behavior data representing shapes of the heart at different time steps of a behavioral simulation to mimic the motion of the heart beating, and electrocardiogram data representing temporal variations of an electrical signal in myocardium that have been measured from the patient; and a processor configured to perform a procedure including:

determining, based on the shapes represented in the heart behavior data, a first time step at which atriums of the heart begin to contract in accordance with a beginning of a P wave of the electrical signal appearing in an electrocardiogram, as well as a second time step at which ventricles of the heart begin to contract in accordance with a beginning of a QRS complex of the electrical signal appearing in the electrocardiogram, the QRS complex including an R wave, a first shape, represented in the heart behavior data, at the first time step including a shape of the atriums starting to move to contract the atriums from a position of the atriums before a heart beat begins, and a second shape, represented in the heart behavior data, at the second time step indicating a shape of the ventricles starting to move to contract the ventricles from a position of the ventricles before the heart beat begins, and reproducing behavior of the heart over time by updating the three-dimensional model according to the heart behavior data, simultaneously with variations in strength of the electrical signal over time according to the electrocardiogram data, such that the first shape of the heart, represented in the heart behavior data, at the first time step is reproduced simultaneously with a peak of the P wave delayed from the beginning of the P wave, and such that the second shape of the heart, represented in the heart behavior data, at the second time step is reproduced simultaneously with a peak of the R wave delayed from the beginning of the QRS complex, wherein the first time step is a time step at which an initial move of atrial myocardium is detected at an intersection point of a first straight line traversing atriums of the heart and a free wall of the atriums, the first straight line being perpendicular to an axis and apart from a line segment at a first distance, the line segment being drawn between a center of an aorta valve and a center of a mitral valve, the axis passing through a midpoint of the line segment and a bottommost ventricular point, and the second time step is a time step at which an initial move of ventricular myocardium is detected at an intersection point of a second straight line traversing ventricles of the heart and a free wall of the ventricles, the second straight line being perpendicular to the axis and apart from a third straight line at a second distance, the third straight line being perpendicular to the axis and passing through the bottommost ventricular point.

2. The visualization apparatus according to claim 1, wherein the reproducing behavior of the heart includes:

dividing a single heart beat cycle into first to third sections, the first section being a period from a start of the electrical signal that initiates the single heart beat cycle to the peak of the P wave, the second section being a period from the peak of the P wave to the peak of the R wave, the third section being a period from the peak of the R wave to an end of the electrical signal that terminates the single heart beat cycle; and determining at what constant time intervals the processor is to reproduce the shapes of the heart at different time steps, depending on to which of the first to third sections of the single heart beat cycle the different time steps belong.

3. A visualization method comprising:

determining, by a processor, a first time step at which atriums of a heart begin to contract in accordance with a beginning of a P wave of the electrical signal appearing in an electrocardiogram, as well as a second time step at which ventricles of the heart begin to contract in accordance with a beginning of a QRS complex of the electrical signal appearing in the electrocardiogram, the QRS complex including an R wave, based on heart behavior data representing shapes of the heart at different time steps of a behavioral simulation to mimic the motion of the heart beating, a first shape, represented in the heart behavior data, at the first time step including a shape of the atriums starting to move to contract the atriums from a position of the atriums before a heart beat begins, and a second shape, represented in the heart behavior data, at the second time step indicating a shape of the ventricles starting to move to contract the ventricles from a position of the ventricles before the heart beat begins; and reproducing, by the processor, behavior of the heart over time by updating a three-dimensional model of the heart according to the heart behavior data, simultaneously with variations in strength of an electrical signal over time according to electrocardiogram data representing temporal variations of the electrical signal that have been measured from the patient, such that the first shape of the heart, represented in the heart behavior data, at the first time step is reproduced simultaneously with a peak of the P wave delayed from the beginning of the P wave, and such that the second shape of the heart, represented in the heart behavior data, at the second time step is reproduced simultaneously with a peak of the R wave delayed from the beginning of the QRS complex, wherein the first time step is a time step at which an initial move of atrial myocardium is detected at an intersection point of a first straight line traversing atriums of the heart and a free wall of the atriums, the first straight line being perpendicular to an axis and apart from a line segment at a first distance, the line segment being drawn between a center of an aorta valve and a center of a mitral valve, the axis passing through a midpoint of the line segment and a bottommost ventricular point, and the second time step is a time step at which an initial move of ventricular myocardium is detected at an intersection point of a second straight line traversing ventricles of the heart and a free wall of the ventricles, the second straight line being perpendicular to the axis and apart from a third straight line at a second distance, the third straight line being perpendicular to the axis and passing through the bottommost ventricular point.

4. A non-transitory computer-readable medium storing a program which causes a computer to perform a procedure comprising:

determining a first time step at which atriums of a heart of a patient begin to contract in accordance with a beginning of a P wave of the electrical signal appearing in an electrocardiogram, as well as a second time step at which ventricles of the heart begin to contract in accordance with a beginning of a QRS complex of the electrical signal appearing in the electrocardiogram, the QRS complex including an R wave, based on heart behavior data representing shapes of the heart at different time steps of a behavioral simulation to mimic the motion of the heart beating, a first shape, represented in the heart behavior data, at the first time step including a shape of the atriums starting to move to contract the atriums from a position of the atriums before a heart beat begins, and a second shape, represented in the heart behavior data, at the second time step indicating a shape of the ventricles starting to move to contract the ventricles from a position of the ventricles before the heart beat begins; and reproducing behavior of the heart over time by updating a three-dimensional model of the heart according to the heart behavior data, simultaneously with variations in strength of the electrical signal over time according to electrocardiogram data representing temporal variations of an electrical signal that have been measured from the patient, such that the first shape of the heart, represented in the heart behavior data, at the first time step is reproduced simultaneously with a peak of the P wave delayed from the beginning of the P wave, and such that the second shape of the heart, represented in the heart behavior data, at the second time step is reproduced simultaneously with a peak of the R wave delayed from the beginning of the QRS complex, wherein the first time step is a time step at which an initial move of atrial myocardium is detected at an intersection point of a first straight line traversing atriums of the heart and a free wall of the atriums, the first straight line being perpendicular to an axis and apart from a line segment at a first distance, the line segment being drawn between a center of an aorta valve and a center of a mitral valve, the axis passing through a midpoint of the line segment and a bottommost ventricular point, and the second time step is a time step at which an initial move of ventricular myocardium is detected at an intersection point of a second straight line traversing ventricles of the heart and a free wall of the ventricles, the second straight line being perpendicular to the axis and apart from a third straight line at a second distance, the third straight line being perpendicular to the axis and passing through the bottommost ventricular point.

* * * * *